(12) United States Patent
Ermilov et al.

(10) Patent No.: US 10,709,333 B2
(45) Date of Patent: Jul. 14, 2020

(54) INSTRUMENT FOR ACQUIRING CO-REGISTERED ORTHOGONAL FLUORESCENCE AND PHOTOACOUSTIC VOLUMETRIC PROJECTIONS OF TISSUE AND METHODS OF ITS USE

(71) Applicant: PhotoSound Technologies, Inc., Houston, TX (US)

(72) Inventors: Sergey A. Ermilov, Houston, TX (US); Hans-Peter Brecht, Houston, TX (US); Vassili Ivanov, Houston, TX (US)

( * ) Notice: Subject to any disclaimer, the term of this patent is extended or adjusted under 35 U.S.C. 154(b) by 793 days.

(21) Appl. No.: 15/218,159

(22) Filed: Jul. 25, 2016

(65) Prior Publication Data
US 2018/0020920 A1  Jan. 25, 2018

(51) Int. Cl.
*A61B 5/00* (2006.01)
*A61D 3/00* (2006.01)
(Continued)

(52) U.S. Cl.
CPC .......... *A61B 5/0035* (2013.01); *A61B 5/0013* (2013.01); *A61B 5/0036* (2018.08); *A61B 5/0095* (2013.01); *A61B 5/14546* (2013.01); *A61B 5/4094* (2013.01); *A61B 5/443* (2013.01); *A61B 5/4836* (2013.01);
(Continued)

(58) Field of Classification Search
None
See application file for complete search history.

(56) References Cited

U.S. PATENT DOCUMENTS

2004/0127783 A1* 7/2004 Kruger ................ A61B 5/0059
600/407
2008/0230717 A1* 9/2008 Ashkenazi ......... G01N 21/1702
250/459.1
(Continued)

*Primary Examiner* — Joel F Brutus
(74) *Attorney, Agent, or Firm* — Kurtz Firm, PLLC

(57) ABSTRACT

Disclosed are instruments and methods for acquiring co-registered orthogonal fluorescence and photoacoustic volumetric projections of an interrogated object. In an embodiment, an instrument includes an imaging tank filled with a liquid coupling medium. An object positioning mechanism is configured to position the interrogated object inside the coupling medium and to rotate the interrogated object. An optical excitation unit that is fixed with respect to the tank is configured to induce both fluorescence and photoacoustic responses inside the interrogated object using the same optical excitation spectrum and the same irradiation pattern at the surface of the interrogated object. An array of unfocused photoacoustic transducers is fixed with respect to the tank, and each element of the array is configured to detect photoacoustic signals generated inside the interrogated object. The array is arranged such that a plane connecting the rotation axis and a central portion of the array cuts through the interrogated object separating the two sides irradiated by the optical excitation unit. An optical detector that is fixed with respect to the tank is configured to register planar projections of sources of fluorescence generated inside the object. A data acquisition unit is configured to synchronize acquisition of photoacoustic data, acquisition of fluorescence data, optical excitation, and rotational position of the interrogated object.

39 Claims, 20 Drawing Sheets

(51) Int. Cl.
*A61D 7/04* (2006.01)
*A61B 5/145* (2006.01)
*A61B 5/1455* (2006.01)
*A61B 90/30* (2016.01)
*A61B 90/00* (2016.01)

(52) U.S. Cl.
CPC ............ *A61B 5/4875* (2013.01); *A61B 5/686* (2013.01); *A61B 5/70* (2013.01); *A61D 3/00* (2013.01); *A61D 7/04* (2013.01); *A61B 5/14556* (2013.01); *A61B 2090/306* (2016.02); *A61B 2090/364* (2016.02); *A61B 2503/40* (2013.01); *A61B 2503/42* (2013.01); *A61B 2562/146* (2013.01); *A61B 2562/185* (2013.01); *A61B 2576/00* (2013.01)

(56) References Cited

U.S. PATENT DOCUMENTS

| | | | | |
|---|---|---|---|---|
| 2009/0220430 | A1* | 9/2009 | Rajopadhye | A61K 49/0032 424/9.6 |
| 2010/0249570 | A1* | 9/2010 | Carson | A61B 5/0059 600/407 |
| 2011/0306865 | A1* | 12/2011 | Thornton | A61B 5/0059 600/407 |
| 2012/0220851 | A1* | 8/2012 | Razansky | A61B 5/0073 600/407 |
| 2013/0078625 | A1* | 3/2013 | Holmes | G01N 35/0092 435/6.11 |
| 2013/0190595 | A1* | 7/2013 | Oraevsky | A61B 5/0095 600/407 |

\* cited by examiner

INSTRUMENT FOR ACQUIRING CO-REGISTERED ORTHOGONAL FLUORESCENCE AND PHOTOACOUSTIC VOLUMETRIC PROJECTIONS OF TISSUE AND METHODS OF ITS USE

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The invention generally relates to the field of imaging of small animal biomedical models. Specifically, the invention relates to devices and methods that provide images of internal structures, molecular composition, and functional processes inside a live body based on intrinsic or induced photoacoustic or fluorescent contrast.

BACKGROUND

Non-invasive imaging techniques are extensively used in development and characterization of small animal models of human disease as well as in discovery and evaluation of new therapeutics during pre-clinical studies. A large-scale volumetric imaging mode (whole body imaging) is extremely efficient for those tasks, since it allows simultaneous assessment of multiple regions and organs within the studied organism. Some well-established devices for in vivo imaging employ fluorescent methods and allow affordable, convenient, and highly sensitive interrogation of molecular microenvironments and physiological processes. However, at the same time, those devices suffer from poor spatial resolution, lack abilities to acquire high-fidelity volumetric images and reliable anatomical references. Additional high-resolution 3D imaging modalities, such as computed tomography (CT) and magnetic resonance imaging (MM) are frequently co-employed with fluorescence to assist in robust volumetric mapping of molecular specific information over anatomical structures of the animal. However, the instrumentation and imaging methods utilized in those add-on technologies operate on physical principles and require engineering solutions, which are completely different from the parent optical-type imaging, presenting significant technological and commercial barriers for multi-modal implementation. Attempts have been also made to improve the spatial fidelity of fluorescence images via tomographic reconstruction (fluorescence molecular tomography or FMT). However, low sensitivity, great complexity and slow image acquisition make those tomographic solutions impractical for the modern demands of high-throughput animal studies. Photoacoustic tomography (PAT) is an emerging hybrid biomedical imaging modality combining molecular contrast of optical imaging with high resolution of ultrasound. PAT of live mice was shown to provide high fidelity 3D anatomical maps of skin, vascular tree, and blood rich organs (kidney, spleen, liver, intestine, and heart) with less than 1 minute scans. However, due to strong background signals generated by native blood, its sensitivity to detection of fluorophores is inferior as compared to conventional fluorescence techniques. PAT is attractive from a perspective of its combination with fluorescence imaging, since it can use the same instrumentation for excitation of fluorescence and generation of photoacoustic effect. Combinations of FMT and PAT have been proposed with attempt to further improve accuracy of FMT images. However, those disclosed modalities still failed to sufficiently address problems of slow data acquisition, low sensitivity and inadequate anatomical registration.

SUMMARY

In an embodiment, the disclosed instruments and methods utilize an arrangement of excitation/detection components that allows acquisition of co-registered orthogonal photoacoustic and fluorescence projections of an interrogated biological object, which when collected at multiple angles around the interrogated object may be reconstructed into high-fidelity anatomical references and volumetric maps of fluorophores with significantly improved sensitivity and scan times. Such an instrument can have a transformative impact on the entire field of small animal research, making in vivo characterization of animal models a less costly, faster, more convenient and accurate high-throughput routine. The instrument enables high in vivo resolution and sensitivity for volumetric visualization of native chromophores (hemoglobin, oxyhemoglobin, melanin, water, lipids) and molecular signatures of pathological processes and malformations labeled with fluorophores, organic, plasmonic and carbon nanoparticles, quantum dots, or other photosensitive constructs developed for in vivo tracking, mapping, and longitudinal studies.

In an embodiment, an instrument is disclosed that is capable of acquiring simultaneous photoacoustic and fluorescence orthogonal projections at each rotational position of a biological object. Volumetric images showing distribution of fluorophores inside the interrogated biological object and registered with respect to robust anatomical fiducials can be built from the data acquired by such instrument by performing tomographic reconstruction from the acquired orthogonal projections. The instrument can be optionally upgraded with the following disclosed features: animal restrainer; life support unit; monitoring of temperature in the coupling medium; monitoring of the animal's vital parameters; monitoring of the optical excitation energy; adjustment of the photoacoustic dynamic range; additional continuous wave optical excitation unit, photoacoustic skin visualization unit; photoacoustic array configured for simultaneous detection of low and high frequency wave components; local or remote data processing unit; display unit.

In an embodiment, a method for using the instruments provides collection of multiple co-registered photoacoustic and fluorescence orthogonal projections of the interrogated object with the optical excitation spectra set overlapping with the optical absorption spectrum of each selected fluorophore and the spectral sensitivity of the fluorescence detection unit adjusted to match exclusively the fluorescence emission spectrum of the fluorophore. Further optional upgrades of the data collection method are disclosed that allow: collection of photoacoustic, fluorescent, and surface data from the interrogated object using two sequential scans; acquisition of multiwavelength photoacoustic/fluorescence data using either sequential scans with plurality of excitation spectra or by sweeping the excitation spectrum within a single scan.

In an embodiment, a method for reconstructing images of fluorophores inside the interrogated object using the fluorescence and photoacoustic data collection methods employs fluorescence molecular tomography with emission-only photon propagation model and volumetric distribution of optical fluence at the excitation wavelength of each fluorophore obtained from the acquired orthogonal photoacoustic projections. Further optional upgrades of the reconstruction method are disclosed that additionally inform the photon propagation model with: a multi-domain optical segmentation utilizing the collected orthogonal photoacoustic and surface (skin) data; distribution of optical absorption coefficient utilizing orthogonal photoacoustic data collected at the emission wavelength of each fluorophore.

In an embodiment, another method for reconstructing images of fluorophores inside the interrogated object using the orthogonal fluorescence and photoacoustic data collection methods is disclosed that employs a photoacoustic spectral unmixing algorithm spatially constrained to fluorescent volumes reconstructed using volumetric fluorescence imaging.

BRIEF DESCRIPTIONS OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention. The disclosed embodiments are illustrated by way of example and not limitation in the figures of the accompanying drawings in which like references indicate similar elements.

Figure 1A:
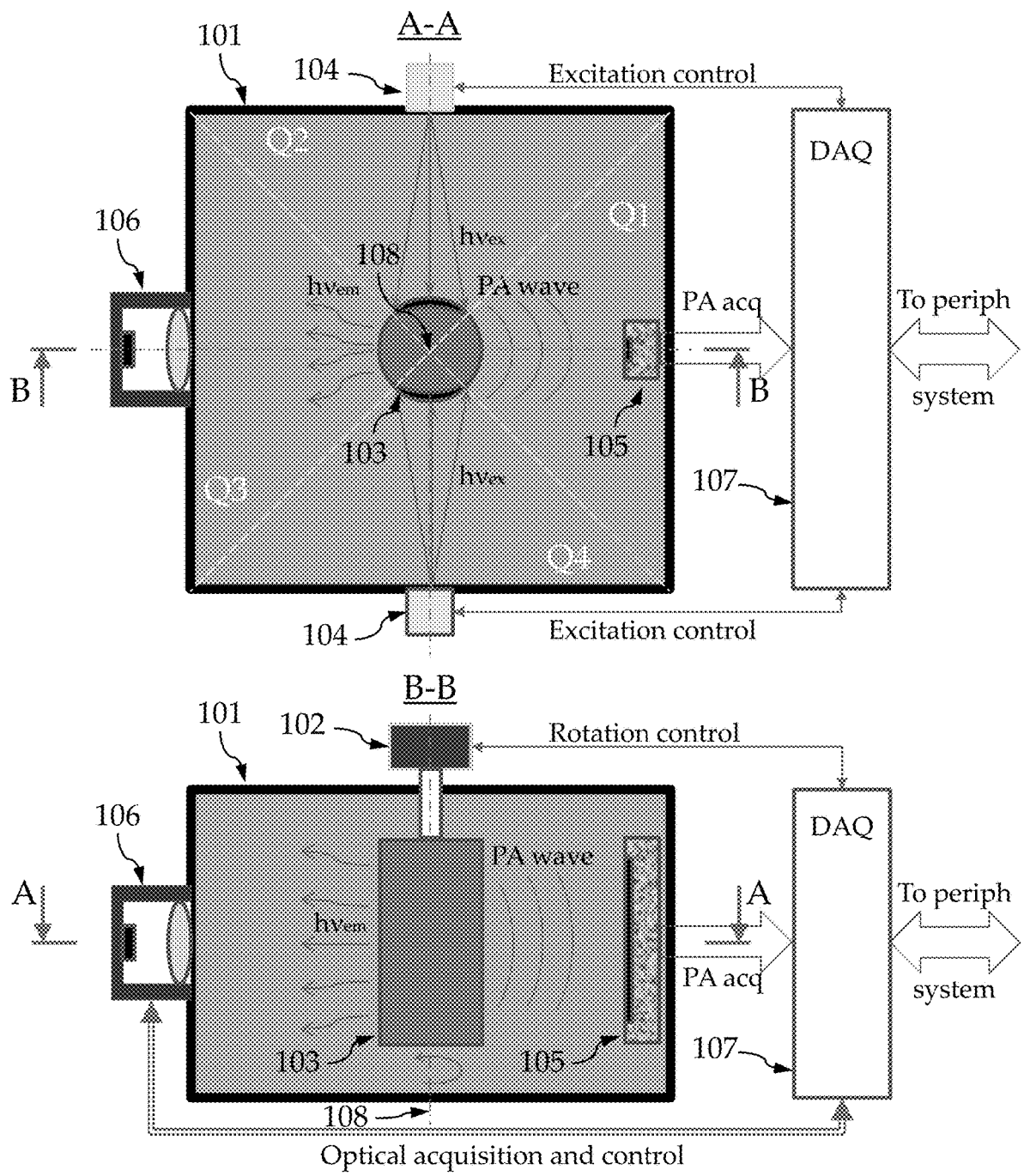
FIG. 1A shows a schematic of the instrument allowing acquisition of co-registered fluorescence and photoacoustic orthogonal volumetric projections of the interrogated biological object.
Figure 1B:
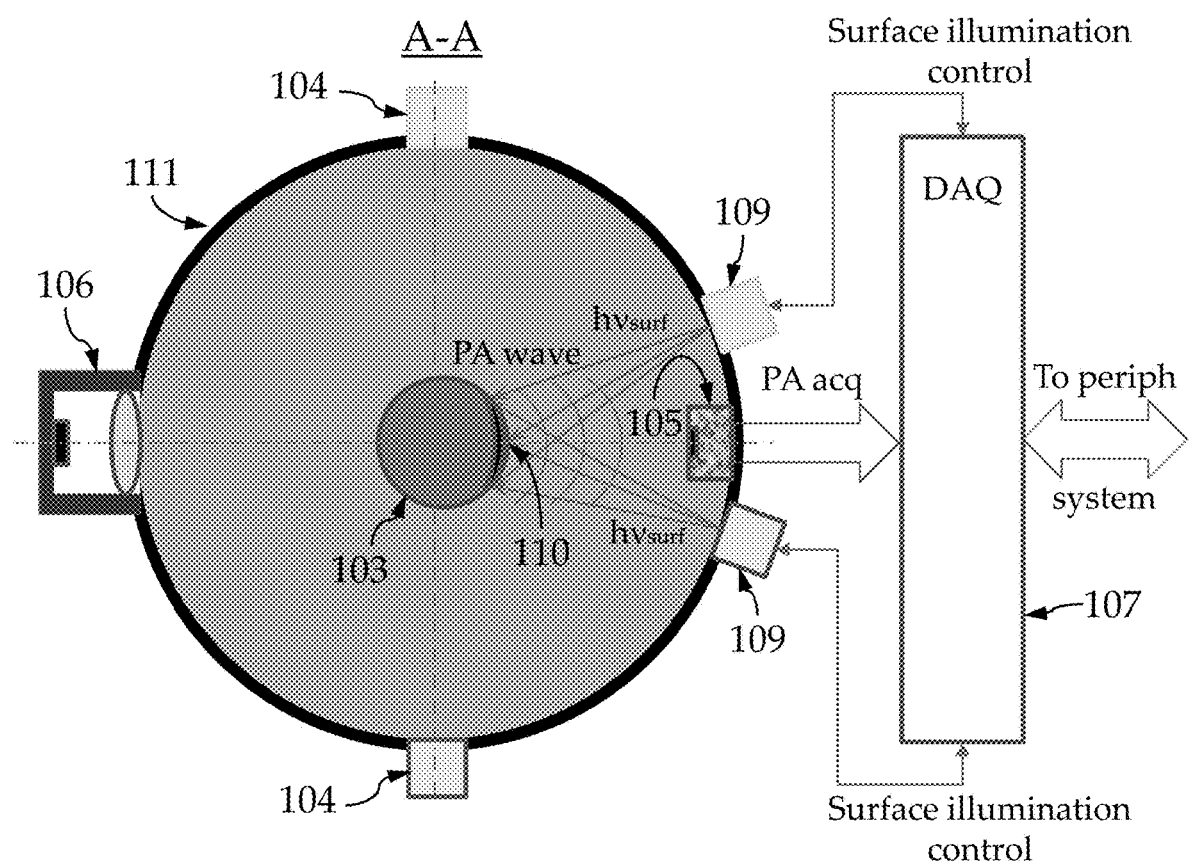
FIG. 1B shows an optional modification enabling an additional photoacoustic channel for visualization of surface (skin) of the interrogated biological object.
Figure 1C:
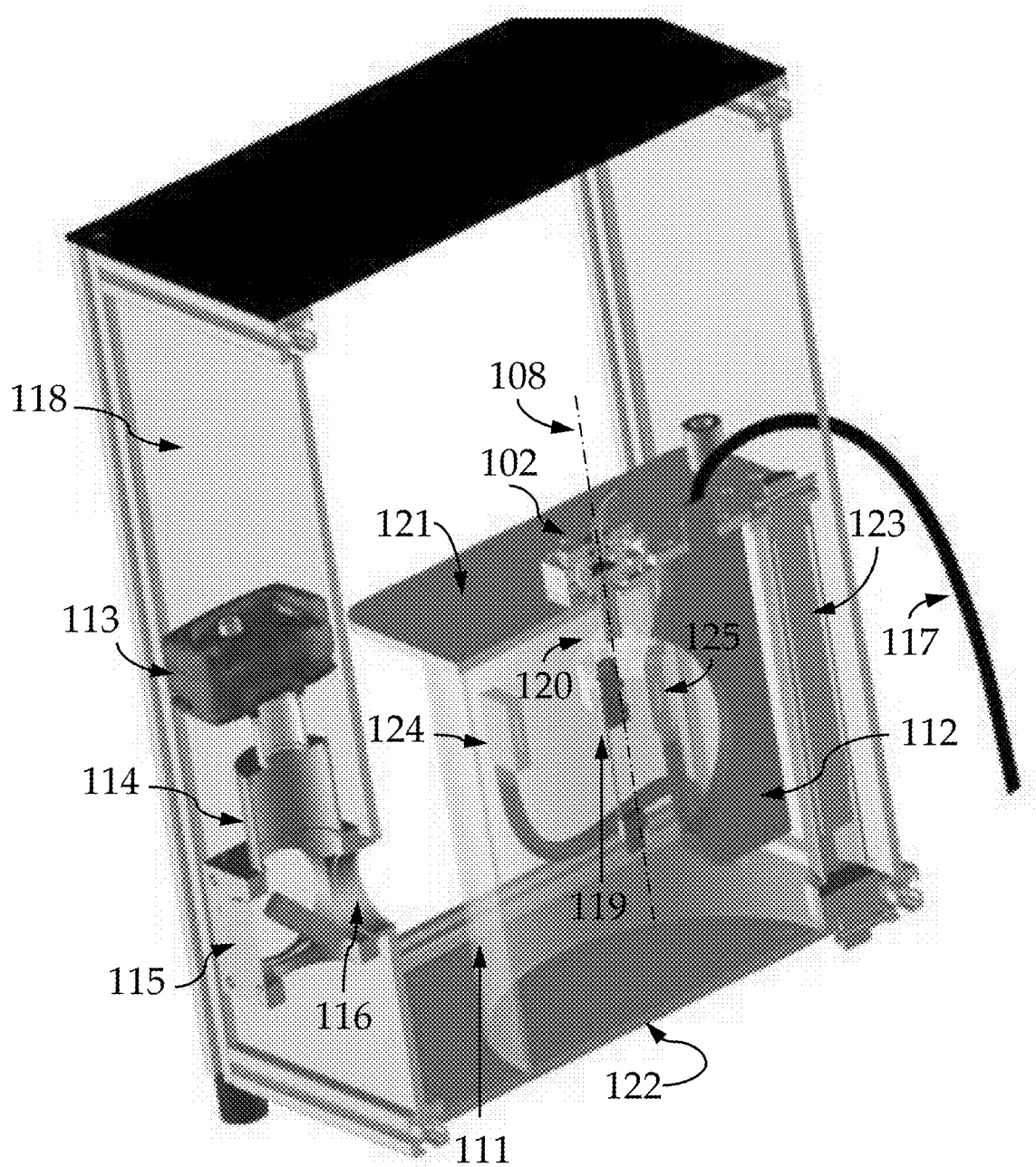

FIG. 1C displays a three-dimensional view of an embodiment of the instrument cut in half with a mid-vertical plane connecting the axis of rotation and midsections of the photoacoustic detector array and the fluorescence imaging unit.

Figure 2A:
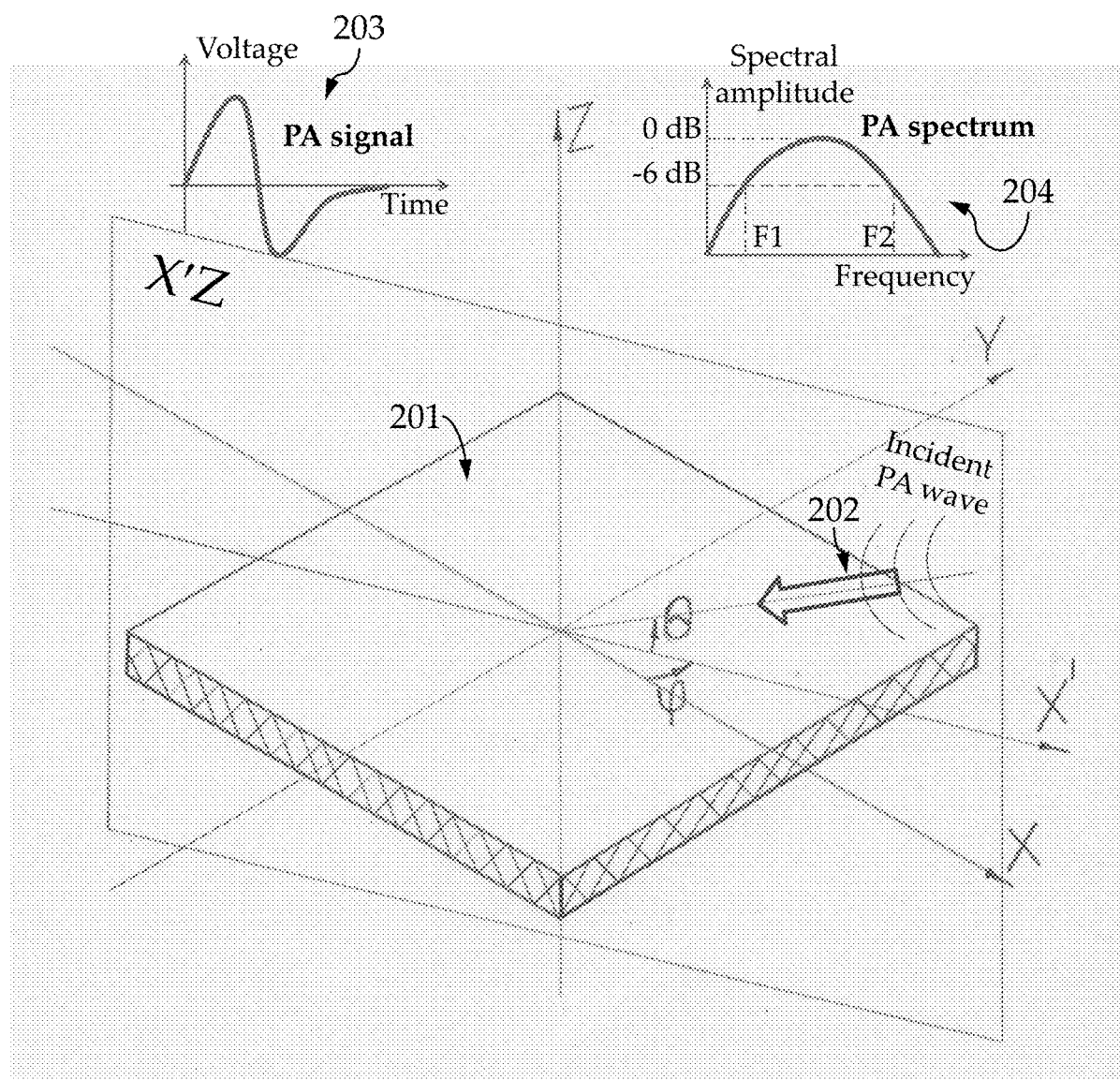

FIG. 2A illustrates the concept of an unfocused photoacoustic transducer, which has substantially similar spectral sensitivity to photoacoustic waves incident upon the transducer from various directions.

Figure 2B:
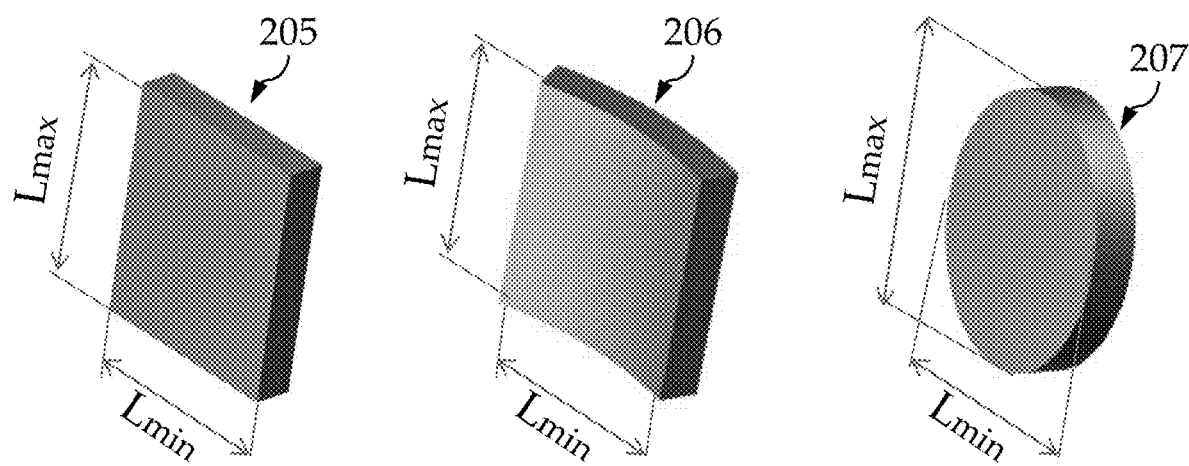

FIG. 2B provides exemplary geometries of individual unfocused photoacoustic transducers, which can be utilized in the photoacoustic array.

Figure 3A:
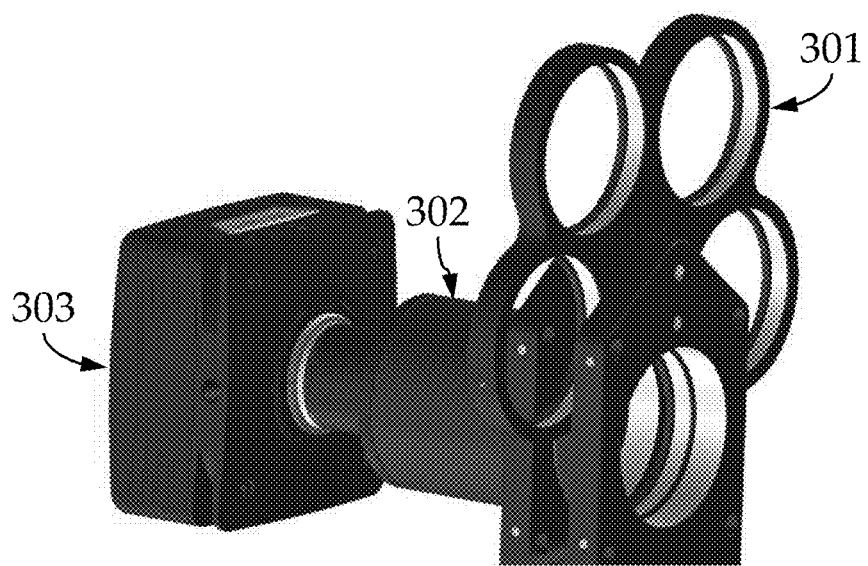
Figure 3B:
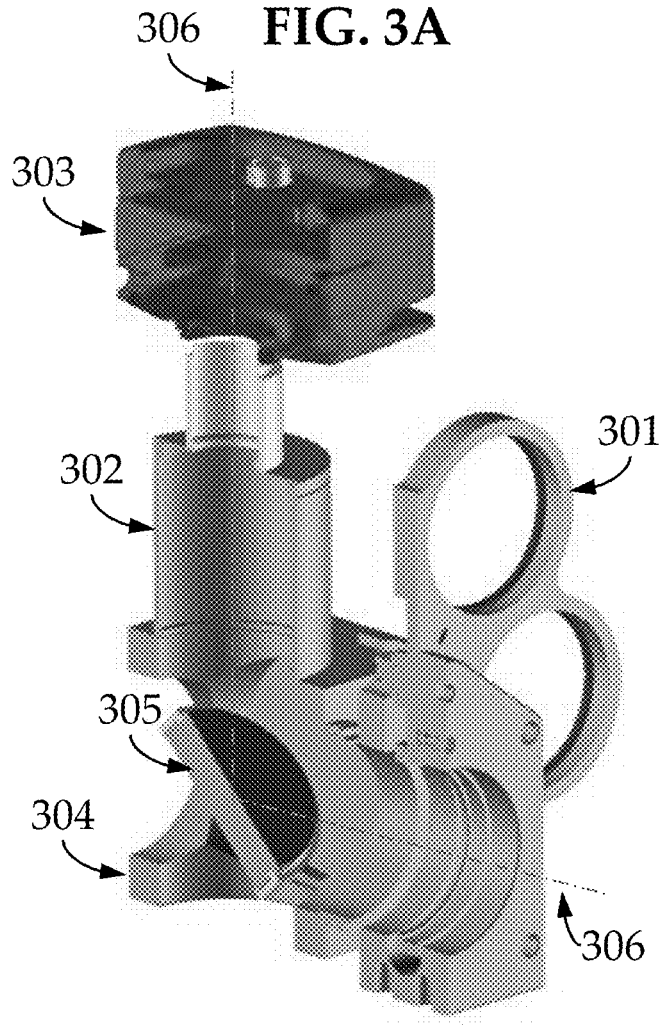

FIGS. 3A and 3B illustrate two embodiments of the fluorescence imaging unit configured to register fluorescence images of the interrogated object.

Figure 4A:
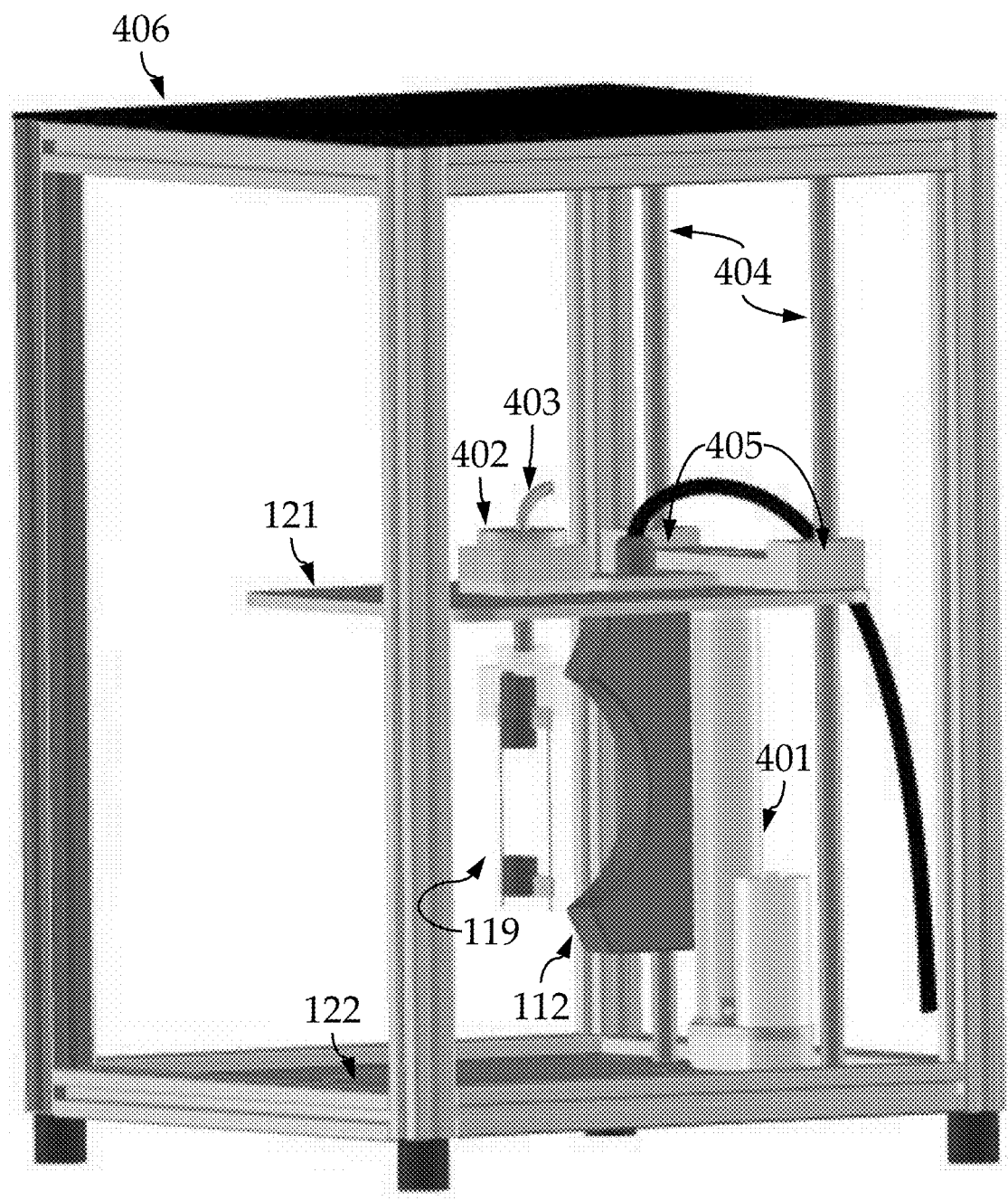

FIG. 4A illustrates an exemplary embodiment of the object positioning mechanism that incorporates a lift system, a rotary stage, an animal gas anesthesia line, and a restrainer.

Figure 4B:
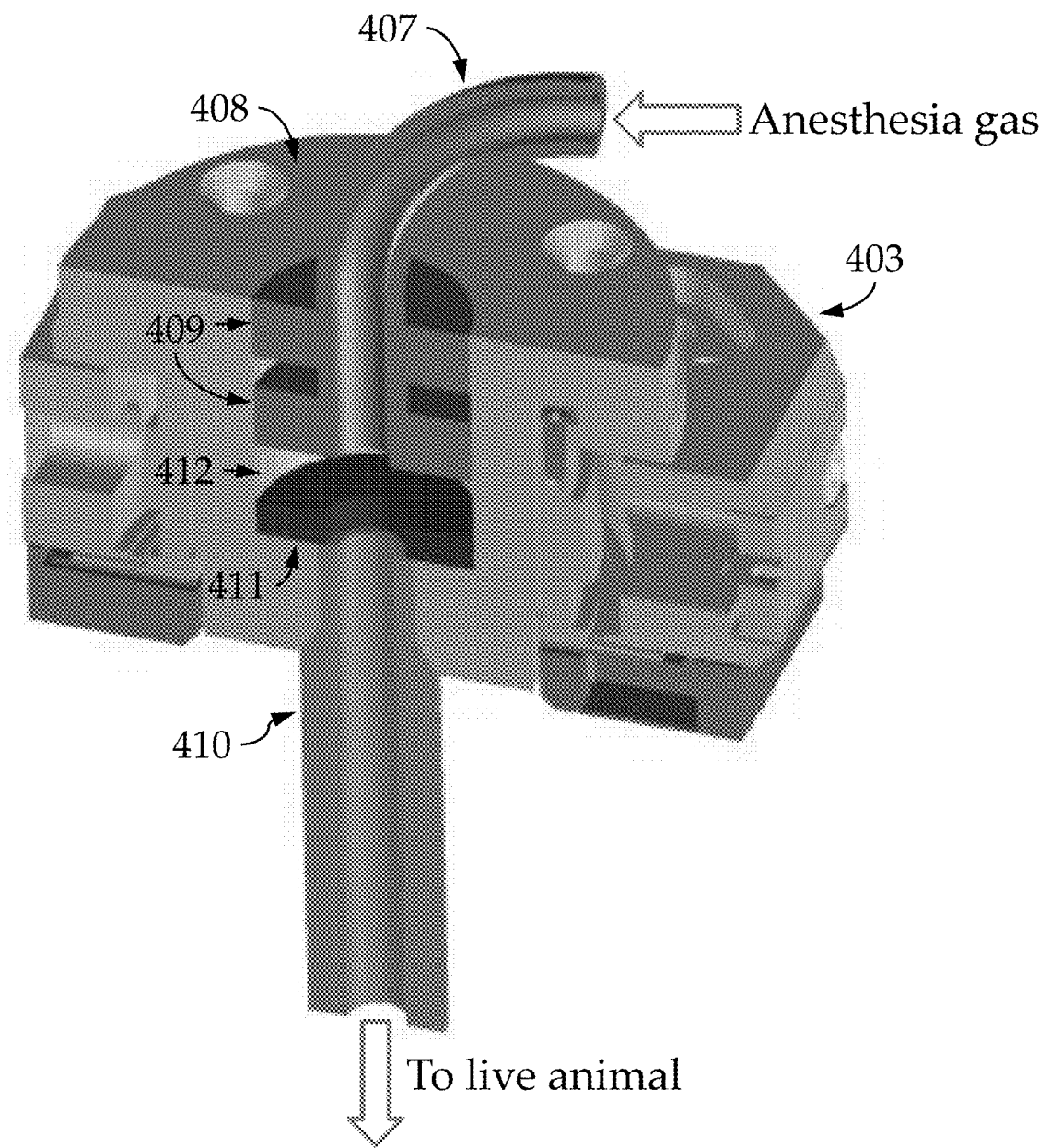

FIG. 4B shows a mid-vertical section of a rotary stage with an embedded gas anesthesia line.

Figure 4C:
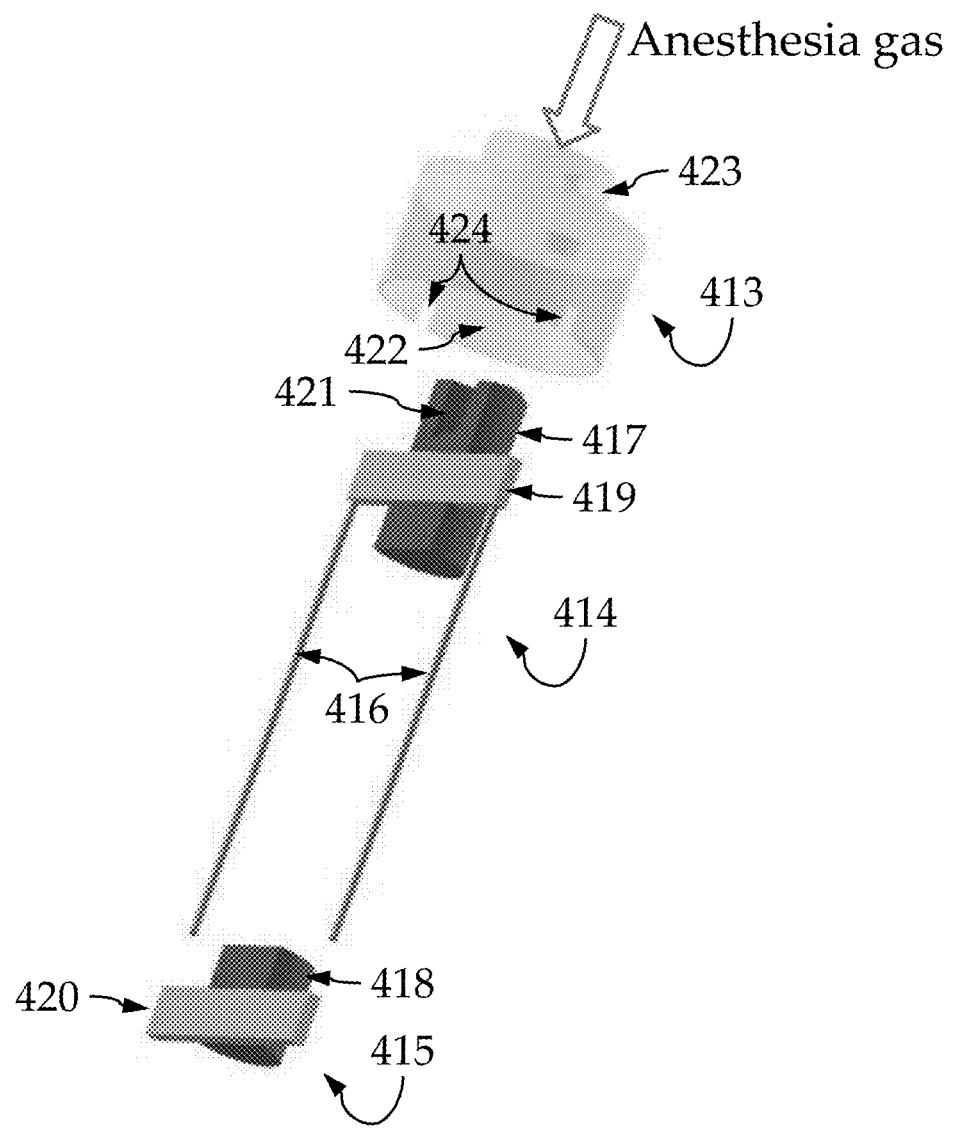

FIG. 4C shows an embodiment of the animal restrainer and its assembly with a submersible positive pressure breathing bell mechanism.

Figure 5:
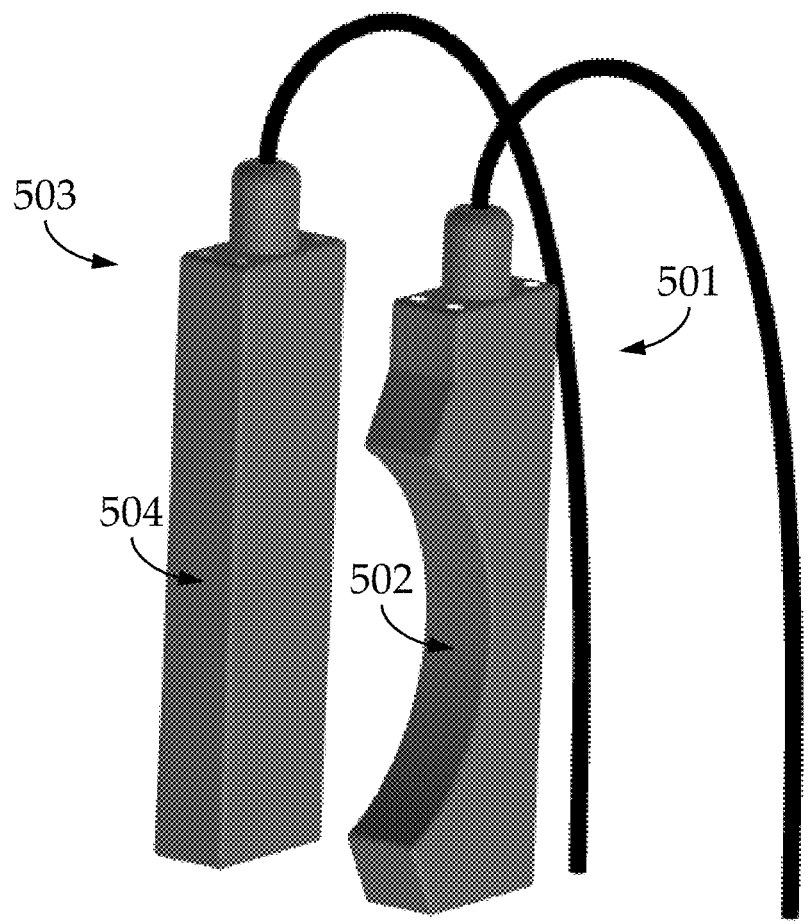

FIG. 5 shows two variants of the photoacoustic array, which can be used in the imaging instrument.

Figure 6A:
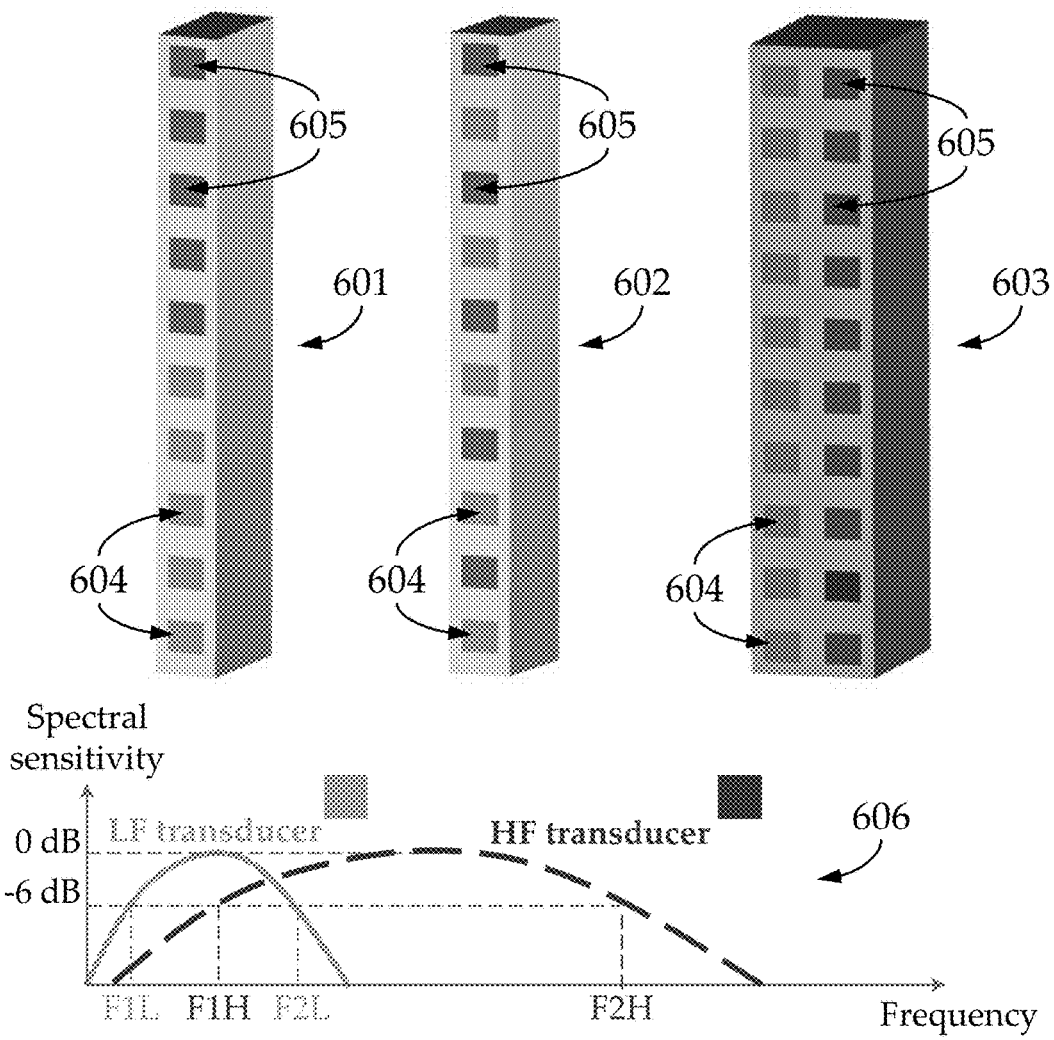

FIG. 6A demonstrates variants of a multi-bandwidth composite photoacoustic array, which can be utilized in the imaging instrument.

Figure 6B:
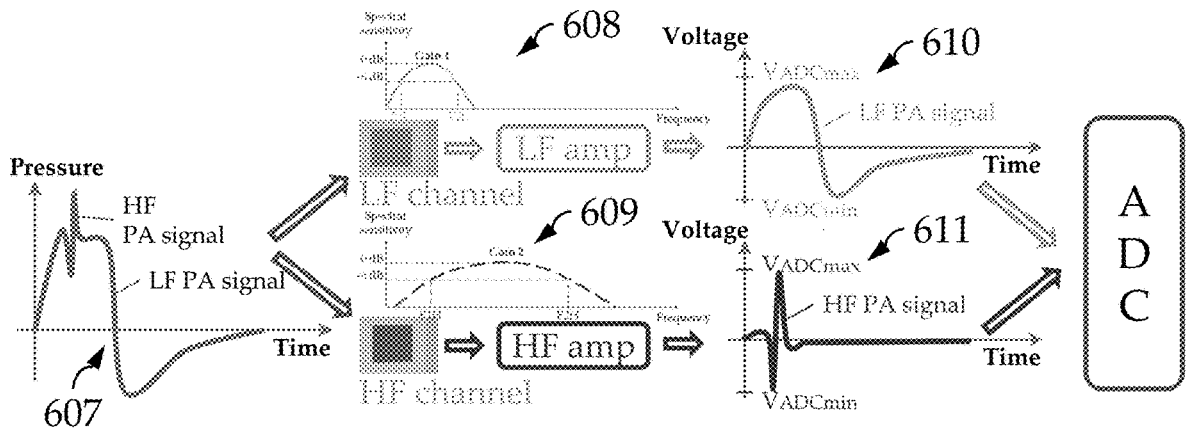

FIG. 6B illustrates how the use of multi-bandwidth detection arrays could be beneficial for expanding dynamic range of a photoacoustic imaging unit for high-frequency signals.

Figure 7A:
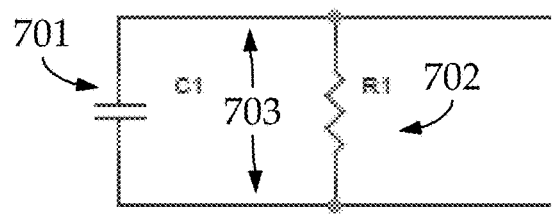

FIG. 7A illustrates an embodiment of a single photoacoustic detection channel with a short electric transmission line.

Figure 7B:
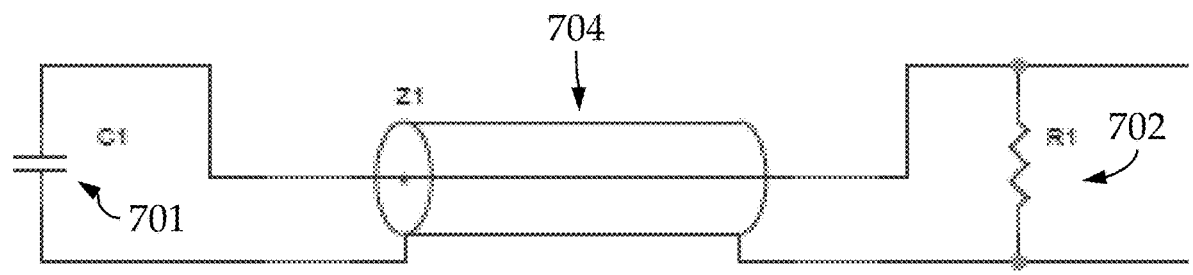

FIG. 7B illustrates an embodiment of a single photoacoustic detection channel with a long electric transmission line.

Figure 8:
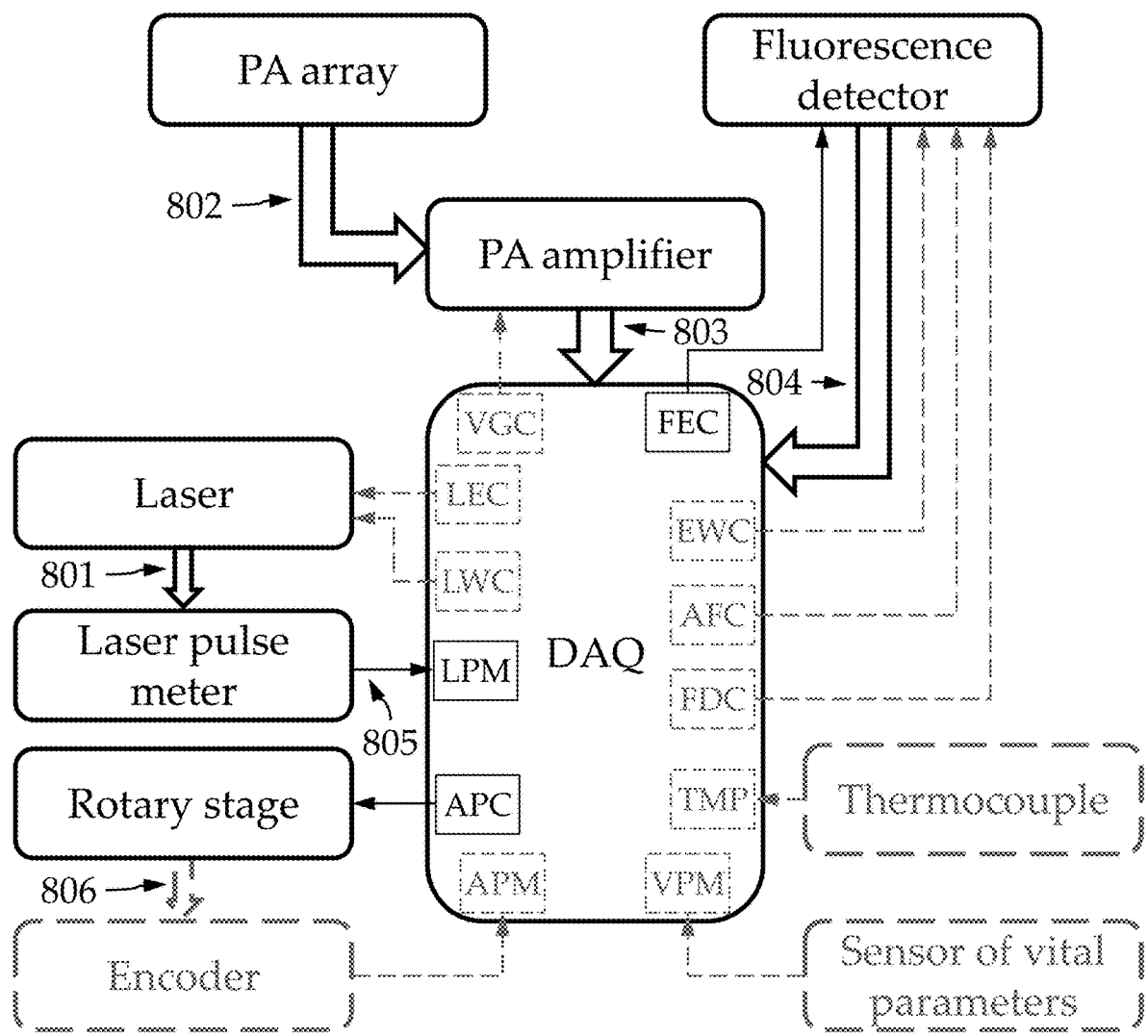

FIG. 8 shows a diagram illustrating a data acquisition unit configured for synchronous collection of orthogonal photoacoustic and fluorescence data, object rotational control, and some optional features including channels for: monitoring/control of optical excitation energy and spectrum, measuring the rotational position, monitoring/control of temperature in the coupling medium, monitoring of animal's vital parameters, control of dynamic ranges for photoacoustic and fluorescence data, control of spectral sensitivity and autofocusing of the fluorescence imaging unit.

Figure 9A:
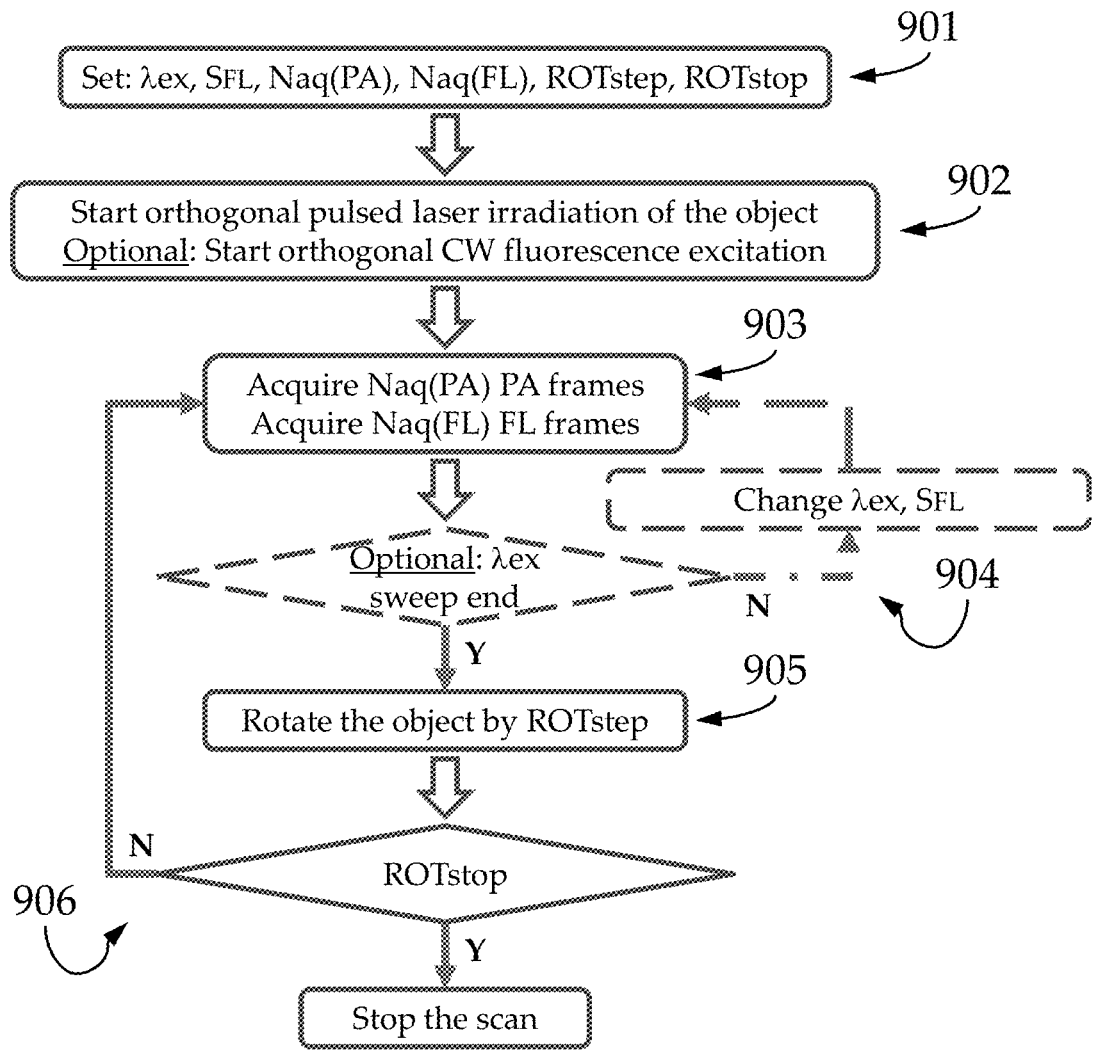

FIG. 9A shows a diagram illustrating methods for collecting co-registered orthogonal photoacoustic and fluorescence data from an interrogated object with step-wise rotational scans.

Figure 9B:
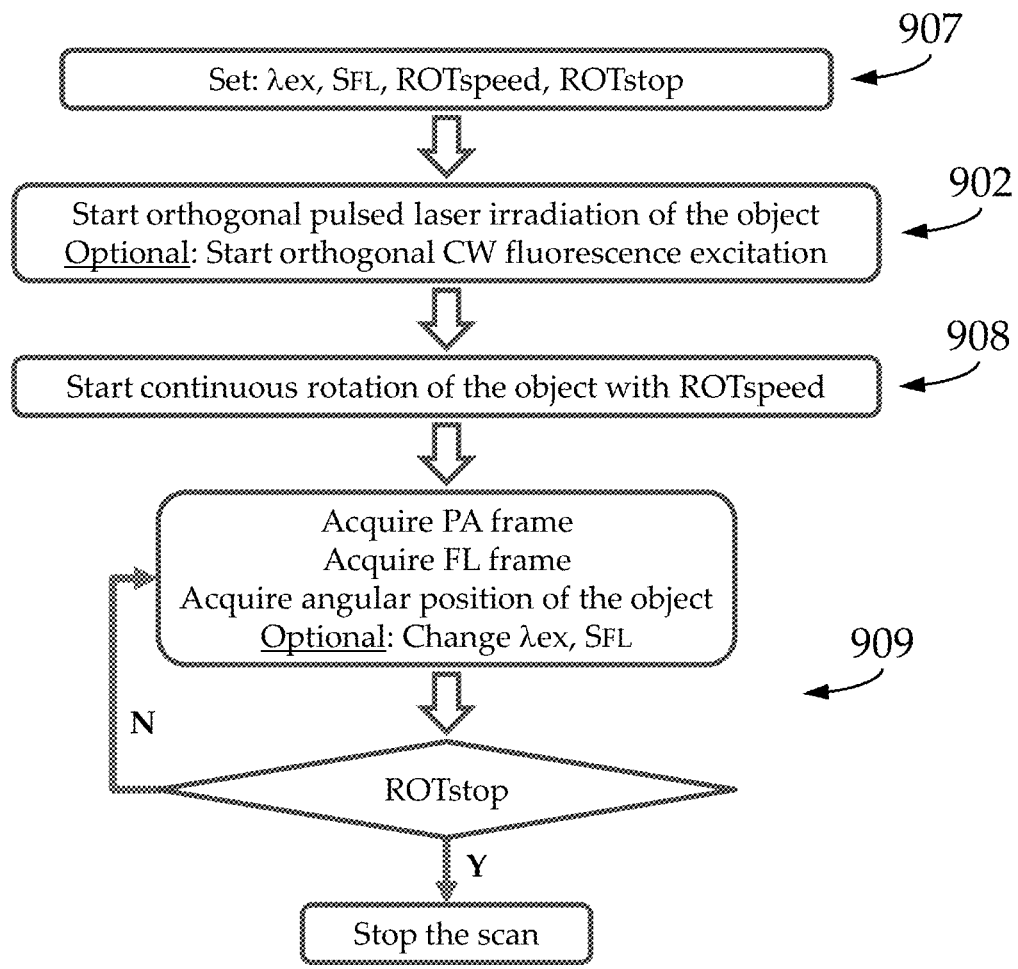

FIG. 9B shows a diagram illustrating methods for collecting co-registered orthogonal photoacoustic and fluorescence data from an interrogated object with continuous rotational scans.

Figure 9C:
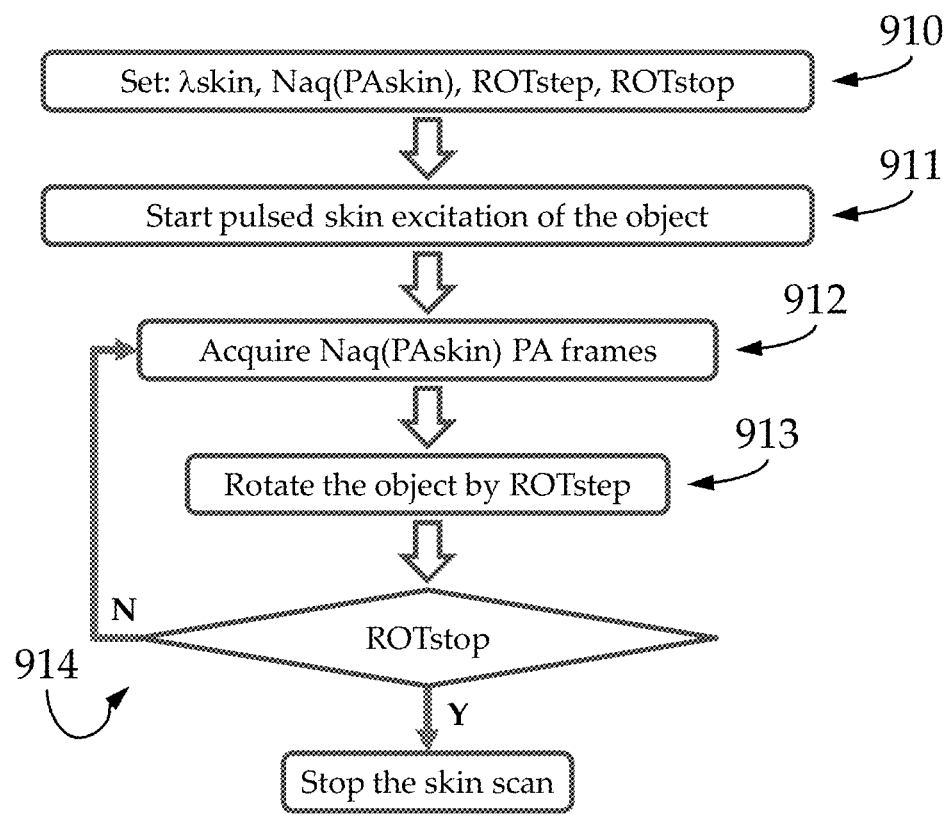

FIG. 9C shows a diagram illustrating methods for collecting photoacoustic surface (skin) data from an interrogated object with step-wise rotational scans.

Figure 9D:
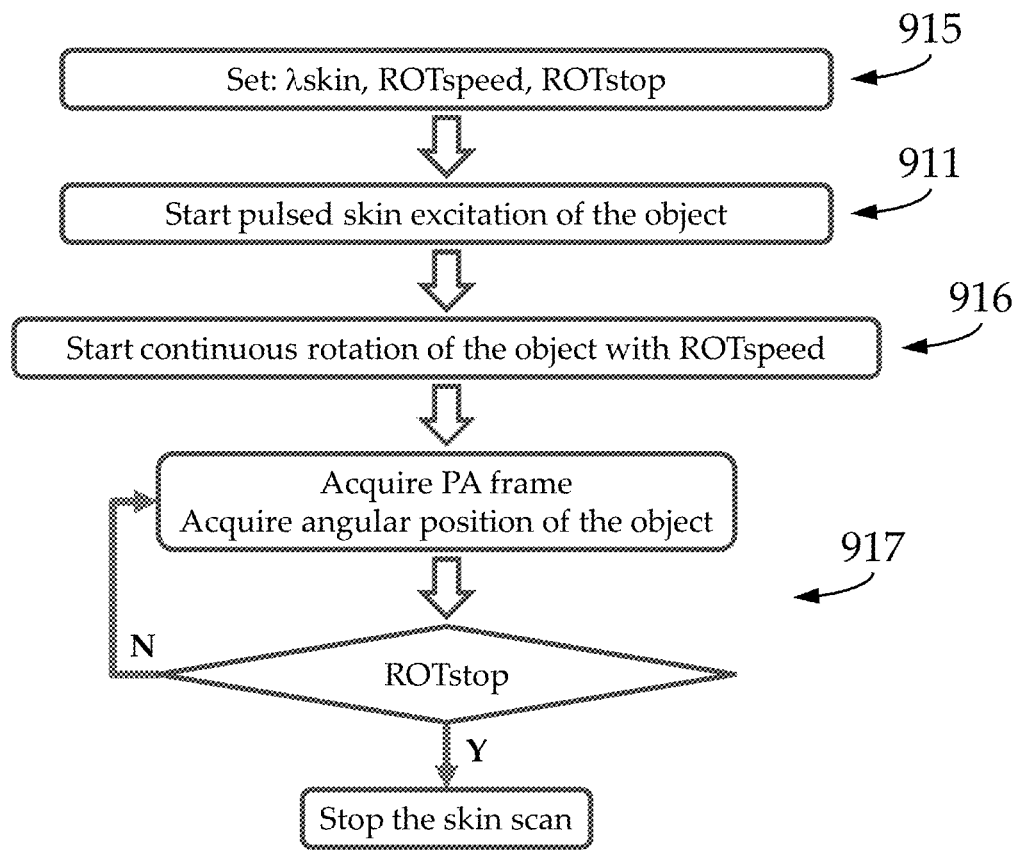

FIG. 9D shows a diagram illustrating methods for collecting photoacoustic skin data from an interrogated object with continuous rotational scans.

Figure 10A:
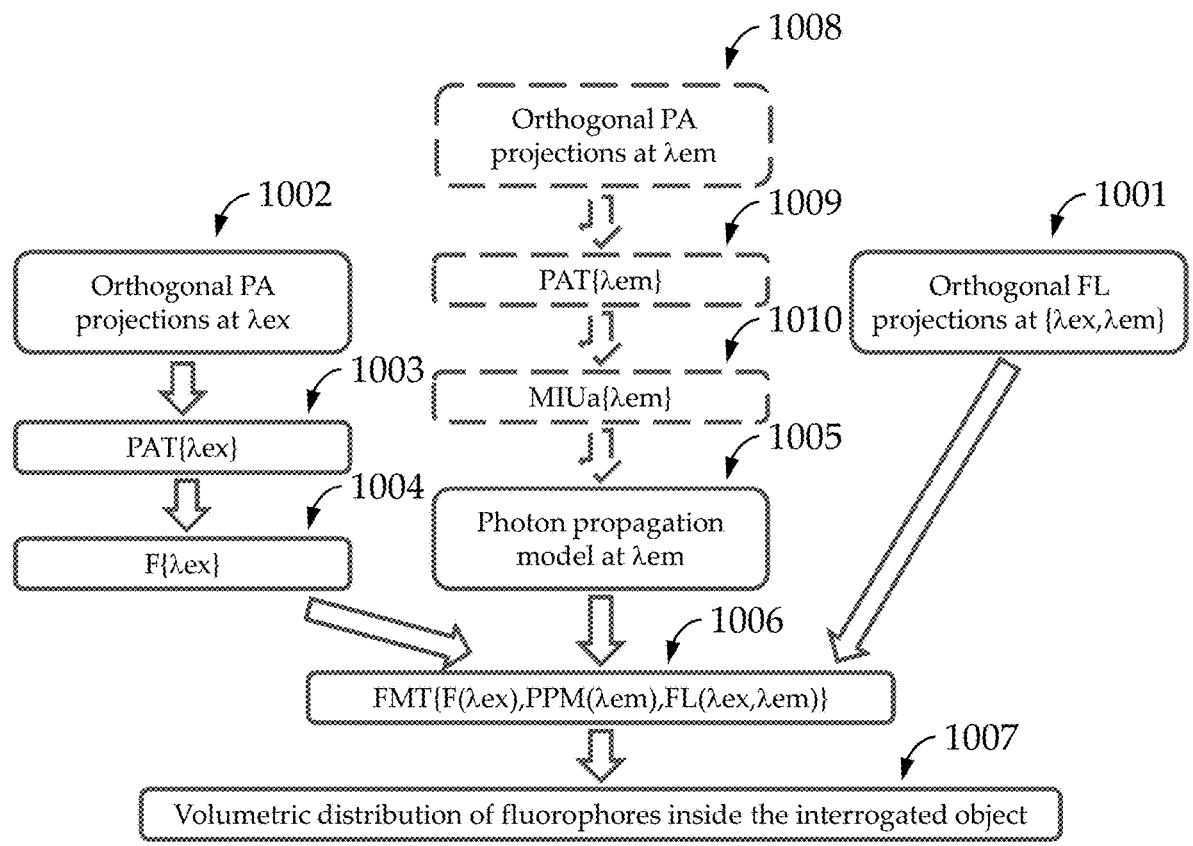

FIG. 10A shows a diagram illustrating methods for reconstructing images of unknown spatial distribution of fluorophores inside an interrogated object using variants of fluorescence molecular tomography with emission-only photon propagation model, photoacoustically reconstructed distribution of optical excitation fluence, and a set of collected orthogonal fluorescence projections.

Figure 10B:
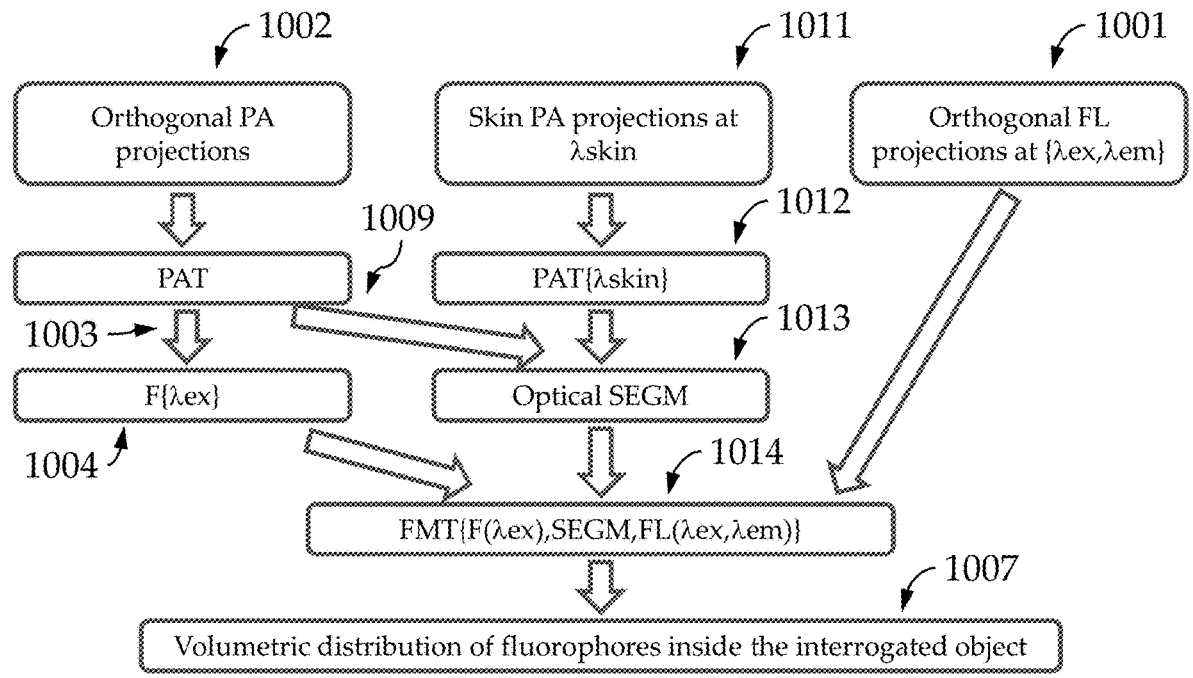

FIG. 10B shows a diagram illustrating methods for reconstructing images of unknown spatial distribution of fluorophores inside an interrogated object using variants of fluorescence molecular tomography with emission-only photon propagation model built on photoacoustic segmentation of the interrogated object, photoacoustically reconstructed distribution of optical excitation fluence, and a set of collected orthogonal fluorescence projections.

Figure 10C:
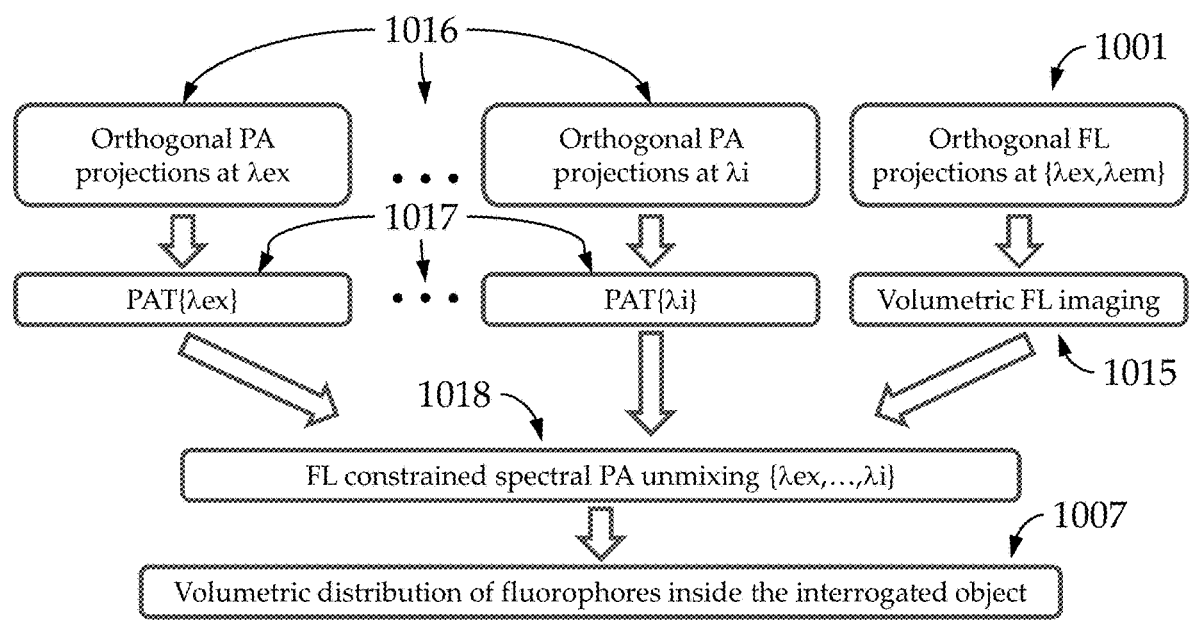

FIG. 10C shows a diagram illustrating method for reconstructing images of unknown spatial distribution of fluorophores inside an interrogated object using fluorescence-constrained photoacoustic spectral unmixing performed on the collected fluorescence and multi-wavelength photoacoustic orthogonal projections.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment, and such references mean at least one.

Reference in this specification to "an embodiment" or "the embodiment" means that a particular feature, structure, or characteristic described in connection with the embodiment is included in at least an embodiment of the disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The present invention is described below with reference to block diagrams and operational illustrations of methods and devices to acquire and process co-registered orthogonal fluorescence and photoacoustic volumetric projections. It is understood that each block of the block diagrams or operational illustrations, and combinations of blocks in the block diagrams or operational illustrations, may be implemented by means of analog or digital hardware and computer program instructions. These computer program instructions may be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein "another" or "other" may mean at least a second or more of the same or different elements or components thereof. The terms "comprise" and "comprising" are used in the inclusive, open sense, meaning that additional elements may be included. As used herein, the term "or" refers to "and/or" unless explicitly indicated to refer to alternatives only or the alternatives are mutually exclusive.

As used herein, the term "about" refers to a numeric value, including, for example, whole numbers, fractions, and percentages, whether or not explicitly indicated. The term "about" generally refers to a range of numerical values (e.g., ±25% of the recited value unless explicitly stated otherwise) that one of ordinary skill in the art would consider approximately equal to the recited value (e.g., having the same function or result). In some instances, the term "about" may include numerical values that are rounded to the nearest significant digit.

The term "3D monitor" refers to a device capable of visualizing volumetric rendering of an image. It also includes the required accessories, e.g. 3D goggles.

The term "biomedical imaging" refers to various techniques and processes of creating visual representations of the interior of an animal's or human's body for biological or medical research, diagnostics, therapy or intervention. Examples include: photoacoustic (PA) imaging, fluorescence (FL) imaging, bioluminescence imaging, ultrasound, magnetic resonance imaging (MRI), computed tomography (CT), X-ray imaging, nuclear imaging.

The term "co-registered" is used herein to describe two or more datasets which are acquired from an interrogated object under conditions allowing association of the information, relevant to the object and carried by those datasets, with anatomical, functional, or molecular features of the object with required temporal and spatial accuracy.

The term "effective optical attenuation coefficient" refers to a coefficient ($\mu_{eff}$) that characterizes exponential attenuation of a planar optical wave ($I_0$) in a slab of a medium with thickness z: $1=I_0\exp(-\mu_{eff}z)$. If optical absorption dominates in a medium, then $\mu_{eff}\approx\mu_a$, where $\mu_a$ is the optical absorption coefficient. If forward optical scattering dominates in a medium (like in most biological tissues), then $\mu_{eff}=\sqrt{3\mu_a(\mu_a+\mu_s(1-g))}$, where $\mu_s$ is the optical scattering coefficient, and g is the scattering anisotropy factor.

The term "encoder" as used herein refers to a device that works together with a rotary stage, and is capable of measuring angular position of the stage with respect to an absolute (global) or a user-set (local) home position (zero). The encoder is also designed to represent that measured position in a form of a unique machine-readable code, which can be analyzed by a computer to recover the actual measured value of angular position of the stage.

The term "fluorescent contrast" as used herein refers to a measurable contrast on fluorescence images produced by spatial variance in concentration of a fluorophore.

The term "fluorescence molecular tomography" (FMT) refers to a method of biomedical imaging of an object with distributed fluorescent substance (fluorophore) by means of: (1) illuminating the object using optical excitation spectrum of the fluorophore; (2) detecting, at multiple known locations around the object, the fluorescence photons emitted by the fluorophore; and (3) using the magnitudes of detected fluorescent signals in mathematical tomographic image reconstruction procedure allowing to solve the inverse problem of photon propagation and excitation of fluorescence and aimed to restore original location and magnitude of the fluorescent sources. Usually, an FMT is described by a discrete forward model according to the normalized Born approach. The required system matrix is established using knowledge of the experimental geometry, and it models the light transport through tissue. Because the FMT system matrix is ill-conditioned, various regularized inversion approaches are employed to obtain an estimate of the fluorophore concentration.

A "frame" of an image or data set refers to a collection of simultaneous data obtained from several identical detectors arranged at different spatial locations.

The term "functional process" refers to a biochemical or physiological process occurring in a living body. Examples: oxygenation of erythrocytes, blood or water perfusion of tissue and organs, neuronal activity, vasodilation, tumor growth, thermoregulation, ischemia.

The term "image" refers to a 2D or 3D representation of an object, part of an object or collection of objects; static or recorded and played as a function of time (movie or video).

The term "induced (exogenous) contrast" refers to a contrast of a feature or a region of an image created exclusively due to artificially-modified properties or characteristics of the visualized object. It requires administration of a contrast agent, genetic modification of endogenous molecules or functional processes, or intervention changing chemical or physical properties in a region of a living body. Examples: indocyanine green (ICG)—photoacoustic and fluorescent contrast agent that requires administration into a body; green fluorescent protein (GFP)—fluorescent contrast agent that is used in fluorescence microscopy of genetically modified living cells; tissue coagulation—process of local tissue destruction that induces optical contrast.

The term "internal structure" refers to certain features of animal's anatomy visualized by a particular biomedical imaging technique. Examples: bones, internal organs, blood vessels, tissue layers, cavities, lumens.

The term "intrinsic (endogenous) contrast" refers to contrast of a feature or a region of an image created due to natural unmodified properties and characteristics of the visualized object. Examples: optical and photoacoustic contrast of blood; contrast of soft tissue layers on ultrasound images; contrast of bones on X-ray and CT images.

The term "mobile device" refers to a portable computing device which has capability for data input. Examples include: laptop computer, tablet, smartphone.

The term "multiwavelength PAT" refers to photoacoustic tomography with data acquired separately for two or more different optical spectra (wavelengths) of illumination.

The term "nanosecond-range" refers to a time range between 0.1 and 1000 ns.

The term "orthogonal fluorescence projection" refers to a frame of data obtained: (1) with fluorescence enabled optical imaging system that has a single or multiple primary direction(s) of optical detection (fluorescence imaging axes) (2) from an object irradiated with fluorescence enabling excitation spectrum that has a single or multiple primary directions of optical excitation (fluorescence excitation axes) (3) while any fluorescence imaging axis form with any fluorescence excitation axis an angle, which is close to 90°.

The term "orthogonal photoacoustic projection" refers to frames of data obtained: (1) with photoacoustic detection system that has a single or multiple primary direction(s) of photoacoustic detection (photoacoustic detection axes) (2) from an object irradiated with nanosecond-range optical pulses, which have a single or multiple primary directions of photoacoustic excitation (photoacoustic excitation axes) (3) while any photoacoustic detection axis form with any photoacoustic excitation axis an angle, which is close to 90°.

The term "photoacoustic contrast" refers to measurable contrast on photoacoustic images produced by spatial variance in optical absorption coefficient or thermoelastic efficiency. Example: blood possesses significant photoacoustic contrast in the near infrared (NIR) range, where hemoglobin—a constituent molecule of red blood cells—dominates over other endogenous molecular components in terms of optical absorption.

The term "photoacoustic spectral unmixing" refers to a family of biomedical imaging techniques combining elements of multiwavelength PAT and spectroscopy and enabling visualization of all optically-absorbing substances distributed inside the interrogated object if the substances have known optical absorption spectra.

The term "photoacoustic tomography" or "PAT" refers to a method of biomedical imaging of an interrogated optically absorbing region by means of illuminating the region with nanosecond-range optical pulses, detecting the resulting ultrasound (photoacoustic) stress waves at a variety of known locations around the region, and using the temporal or spectral profiles of the detected PA waves in mathematical tomographic image reconstruction procedure allowing to solve the inverse problem of PA wave propagation and restore original location and magnitude of the induced PA sources. Examples of PAT algorithms: radial back-projection (RBP), filtered back-projection (FBP), time-reversal, delay-and-sum, iterative photoacoustic reconstruction algorithms based on various discrete PAT forward models and regularized inversion approaches (e.g. robust and rapidly converging FISTA algorithms).

The term "primary direction of optical detection" refers to the optical axis or axes of the entire optical detection unit which comprises at least an optical detector and may also comprise other optical components such as image forming components, fibers, filters, diaphragms, mirrors, prisms, beam splitters, parallel plates, and wedges.

The term "primary direction of optical (photoacoustic) excitation" or "optical (photoacoustic) excitation axis" refers to direction of an optical beam incident upon the interrogated object and exciting in the object fluorescence (photoacoustic) effect.

The term "primary direction of photoacoustic detection" or "photoacoustic detection axis" refers to the axis intersecting the center of the sensitive side of a photoacoustic transducer and directed such that any photoacoustic point source, which belongs to the photoacoustic detection axis is sensed with the greatest magnitude as compared to all other equally strong photoacoustic point sources located at the same distance from the center of the sensitive side of the photoacoustic transducer.

The term "segmentation" refers to image processing and analysis allowing unique identification of certain regions (domains) inside the interrogated object using pre-defined characteristics of the object's image or manual selection by a user. Examples: (1) Two-domain segmentation—separating domains inside the animal and outside the animal using skin detection image processing techniques; (2) segmentation of internal organs or blood vessels; (3) segmentation of fluorescent sources using a threshold in fluorescence magnitude.

The term "small animal biomedical models" refers to rodents (mice, rats, hamsters, gerbils, guinea pigs) and rabbits, which are typically used in biomedical research to learn various aspects of animal biology, study diseases and pathological conditions, and develop novel therapeutic agents, methodologies, and interventional medical procedures.

The term "spatial support" refers to conditional modification or constraint of an image forming algorithm that utilizes known information on geometry, location or intensity of certain features of the visualized image.

The term "virtual reality system" refers to the computer-generated simulation of a three-dimensional image or environment that can be interacted with in a seemingly real or physical way by a person using special electronic equipment, such as goggles or a helmet with a screen inside or gloves fitted with sensors.

The term "vital parameters" refers to parameters and characteristics pertinent to and identifying a live body, which can be measured or visualized. Examples: body temperature, breathing, heart rhythm.

In at least some embodiments, the present disclosure is directed to an instrument that allows collection of co-registered photoacoustic and fluorescence orthogonal volumetric projections of an interrogated object. The interrogated object can be represented by a small animal biomedical model.

A significant advantage of orthogonal photoacoustic projections is that they contain minimal information from optical energy absorbed in superficial layers (skin) and bulk of the interrogated object, which otherwise dominates over and masks the signals generated by internal tissues and organs. Generally, photoacoustic wave components produced by excitation of the skin layer and bulk of the interrogated object are characterized by large magnitudes and propagate predominantly along the photoacoustic excitation axis. On the other hand, the excitation photons become scattered inside the interrogated object and irradiate most of the internal structures from various directions inducing quasi-isotropic photoacoustic sources. Therefore, photoacoustic waves from the internal sources propagate in all directions including those toward the photoacoustic transducers, which are arranged orthogonally with respect to the photoacoustic excitation axis, while undesirable waves generated in skin and bulk of the interrogated object propagate along the photoacoustic excitation axis and are never detected by the orthogonally arranged photoacoustic transducers.

A significant advantage of orthogonal fluorescence projections is that they significantly reduce background signals associated with transmitted or backscattered photons, which present a challenge in trans-illumination and epi-illumination configurations of fluorescence, respectively. In the orthogonal configuration of fluorescence, the photons transmitted through and backscattered from the interrogated object will miss the detector's aperture, while omnidirectional sources of fluorescence could be detected well from anywhere around the interrogated object.

FIG. 1A illustrates an embodiment of such instrument (top and side mid-sectional views). The embodiment contains the following components: an imaging tank filled with a coupling medium 101, a positioning and rotary mechanism 102, an interrogated object 103, light emitting termini of the optical excitation unit 104, an array of unfocused photoacoustic transducers 105, a fluorescence imaging unit 106, a data acquisition and control unit (DAQ) 107.

The optical excitation unit 104 is configured to induce both fluorescence and photoacoustic responses inside the interrogated object using the same optical excitation spectrum and the same irradiation pattern at the surface of the interrogated object. An exemplary optical excitation unit 104 may employ a single or multiple sources of optical radiation synchronized to emit simultaneous pulses with the following characteristics: (a) emitted spectrum in the range of 532 nm to 1400 nm; (b) an arbitrary temporal pulse profile and pulse duration less than 100 ns as estimated at the full-width-half-max (FWHM); (c) pulse repetition rate exceeding 0.5 Hz. Examples of such pulsed optical sources include Q-switched Nd:YAG lasers, Ti:Saph lasers, Alexandrite lasers, Optical Parametric Oscillators (OPO) or pulsed diode lasers.

It may also use additional continuous wave (CW) or pulsed optical sources with pulse durations exceeding 100 ns in order to enhance the fluorescence response. Those sources can be incorporated either within the same (primary) optical excitation unit or within additional optical excitation units; however, they must produce the same spectral content and irradiation pattern at the surface of the interrogated object as the primary (pulsed) excitation unit.

Acquisition of orthogonal photoacoustic and fluorescence projections is enabled in such configuration by positioning light emitting termini 104 at angles close to 90° with respect to both the array of photoacoustic transducers 105 and the fluorescence imaging unit 106. In the embodiment depicted in FIG. 1A it is further illustrated that all the crucial light emitting components and the detectors must be arranged in four different orthogonal quadrants (Q1-4) intersecting over the axis of rotation 108. Specifically, the array of photoacoustic transducers 105 is placed in the quadrant Q1, one light emitting terminal 104 is placed in the quadrant Q2, the fluorescence imaging unit 106 is placed in the quadrant Q3 opposite to the array of photoacoustic transducers, and the other light emitting terminal 104 is placed in the quadrant Q4. Although, the embodiment depicted in FIG. 1A shows two light emitting termini 104, a single array of photoacoustic transducers 105, and a single fluorescence imaging unit 106, other embodiments of the present invention may contain any number of those elements as long as they are arranged to satisfy the orthogonality condition for acquisition of photoacoustic and fluorescence projections of the interrogated object. The ideal orthogonality condition is satisfied when all employed photoacoustic transducers and all employed fluorescence detectors have primary directions of detection oriented at 90° with the respective excitation axes (photoacoustic and optical). In practical applications those angles should be maintained at 90°±30° to fully benefit from the advantages of photoacoustic and fluorescence orthogonal projections of the interrogated object.

The imaging tank 101 could be made of an optically transparent material like polycarbonate, acrylic or glass. The coupling medium filling the imaging tank must allow transmission of photoacoustic waves (PA wave) generated inside the interrogated object 103 to the array of photoacoustic transducers 105 without significant energy losses due to absorption, reflection, refraction, and scattering of all the frequency components of the PA wave. Generally, it implies that the coupling medium must be homogeneous in terms of acoustic impedance, have low frequency-dependent acoustic attenuation, and the acoustic impedance of the coupling medium must be close in magnitude to acoustic impedances of the interrogated object and the photoacoustic transducers used in the array 105. Furthermore, the coupling medium must transmit the excitation light ($h\nu_{ex}$) from the light emitting termini 104 to the interrogated object without significant energy losses due to absorption, reflection, refraction, and scattering of optical wavelengths contributing to the fluorescence excitation spectrum. Generally, it implies that the coupling medium should be non-scattering and have low optical absorption within the fluorescence excitation spectrum. Furthermore, the coupling medium must transmit the fluorescence emission light ($h\nu_{em}$) from the interrogated object to the fluorescence detector 106 without significant energy losses due to absorption, reflection, refraction, and scattering of optical wavelengths contributing to the fluorescence emission spectrum. Generally, it implies that the coupling medium should be non-scattering and have low optical absorption within the fluorescence emission spectrum. Optically transparent liquids composed of a single chemical, mixture, solution, suspension, emulsion or gel could be good candidates for the coupling medium. Some examples of good coupling media include: water, aqueous ionic solutions of sodium chloride, and phosphate buffered saline (PBS). For example, specific acoustic impedance of water is about $1.5 \times 10^6$ kg/(m^2*s), while optical absorption coefficient is between 0.007 and 0.064 cm^-1 in the near-infrared range 700-900 nm. Small concentrations of other chemical compounds could be added to the coupling medium, provided they do not change optical and acoustic properties of the coupling medium. Closed loop circulation of the coupling medium with in-line degassing unit can be also implemented to improve thermal and acoustic homogeneity of the coupling medium.

The positioning and rotary mechanism 102 may include a rotary stage operated in a continuous or a stepper mode with an encoder measuring angular position of the interrogated object at each photoacoustic or fluorescence data acquisition event. The positioning and rotary mechanism may further incorporate an animal restrainer, a breathing unit, a gas anesthesia unit, and an intravenous delivery unit.

The DAQ unit 107 is generally configured to synchronize the acquisition of photoacoustic data, fluorescence data, optical excitation, and rotation of the interrogated object. It is further configured to amplify, filter, digitize, and transfer the acquired data to a peripheral system (not shown in FIG. 1A) for subsequent storage, processing, or visualization.

The imaging instrument may be additionally configured with a CW optical illumination unit that operates in a visible spectral range of 400-700 nm and together with the fluorescence imaging unit 106 serves to visually observe the interrogated object.

FIG. 1B shows an embodiment of the instrument with optional modification enabling additional photoacoustic channel for visualization of surface (skin) of the interrogated biological object. The skin imaging photoacoustic channel employs the same array of photoacoustic transducers 105, along with additional reflection-mode photoacoustic skin excitation unit 109. Light emitting termini of the skin excitation unit must be positioned in the same quadrant Q1 as the array of photoacoustic transducers to generate strong and clean photoacoustic signatures of the skin propagated from the illuminated region 110 that directly faces the array of photoacoustic transducers 105. The skin excitation unit may operate in a visible spectral range of 400-700 nm. An alternative cylindrical embodiment of the imaging tank 111 is shown in FIG. 1B.

FIG. 1C displays a three-dimensional view of an embodiment of the instrument cut in half by a mid-vertical plane connecting the axis of rotation 108 and midsections of the arc-shaped photoacoustic detector array 112 and the fluorescence imaging unit. The fluorescence imaging unit illustrated in FIG. 1C is built on a camera sensor 113 with image forming optics 114 and an axis-bending mirror installed in a cube mount equipped with fluorescence emission filters 115. The fluorescence imaging unit views the interrogated object through an orifice in the housing 116. Bending optical axis of fluorescence imaging unit makes the entire instrument more compact.

The embodiment illustrated in FIG. 1C also incorporates fiberoptic light delivery for excitation of fluorescence and photoacoustic response 124 inside the interrogated object and for excitation of the skin photoacoustic response 125. Each of those light delivery units can be implemented using a single input fiberoptic bundle, which is then bifurcated into two output bundles with individual fibers randomized as compared to their original arrangement in the input bundle, and terminated into the required output apertures. The output light emitting termini could be of any shape as long as they allow illumination of the required regions of the interrogated object. The output light emitting termini can be either submerged into the coupling medium or attached to the outside of the imaging tank 111 via optically transparent index matching fluid, gel, or adhesive.

The array of photoacoustic transducers 112 transfers detected signals to a DAQ unit (not shown) over the electrical cable 117. The entire instrument is encased in a housing 118. The parts of the instrument illuminated during a scan can be made of non-fluorescent materials or black-coated to reduce background fluorescence and stray lights. The imaging tank is configured as a cylinder 111 and contains both the interrogated object and the array of photoacoustic transducers 112 submerged in a coupling medium. Alternatively, the array of photoacoustic transducers may have its sensitive face attached to the external surface of the imaging tank via acoustically transparent coupling layer or adhesive.

Generally, the array of photoacoustic transducers must be configured such that each sensor element of the array can detect photoacoustic waves originated in any voxel of the interrogated volume (unfocused transducers). A particular arc-shaped arrangement of the array 112 with the center of the arc located near the center of the interrogated volume allows each sensor element to detect photoacoustic waves generated inside the interrogated volume with the highest accuracy and sensitivity as compared to other possible arrangements. Such arc-shaped arrangement allows each transducer element of the array to have its normal z (FIG. 2A) aimed to the middle of the interrogated volume. In such orientation of transducers, photoacoustic waves generated inside the interrogated volume arrive at each transducer with high elevation angles $\Theta$. Generally, sensitivity of a photoacoustic transducer increases for high elevation angles $\Theta$, while the distortions of registered PA signals decrease.

For those transducers without axial symmetry of the sensitive surface with respect to the normal z, their acousto-electric impulse response (electrical signal generated in response to an instant acoustic pulse or an acoustic delta source) also depends on the azimuth $\varphi$ of the incident photoacoustic wave. Generally, the larger the dimension of a transducer as it is sectioned by the plane of incidence (X'Z in FIG. 2A), the lower in magnitude and the more distorted is the acousto-electric impulse response, which ultimately defines the response of a transducer to any photoacoustic source. A good unfocused (omnidirectional) transducer will have approximately equal dimensions independent of the azimuth of the plane of incidence. It should also have no focusing elements such as large out-of-plane curvatures of its sensitive surface or acoustic lenses. In practice, to achieve good omnidirectional spatial impulse response of a transducer in the far field (distance away from transducer, which is 10 times or more the maximum dimension of the transducer), the ratio of its shortest to its longest dimension across the sensitive area must be no less than 2:3.

FIG. 2A shows an individual planar photoacoustic transducer 201, having the normal Z and the detection plane XY. A photoacoustic wave 202 is incident upon the transducer at an elevation angle $\Theta$ and azimuth $\varphi$ formed between the plane of incidence X'Z and the plane XZ (both are orthogonal with respect to the transducer's surface and the detection plane XY). The inlet 203 shows a typical acousto-electric impulse response of a photoacoustic transducer. For smaller elevation angles $\Theta$, the temporal pulse (PA signal) decreases in amplitude and becomes broader. The inlet 204 shows the spectral content (PA spectrum) of the photoacoustic pulse 203. For smaller elevation angles $\Theta$, the PA spectrum decreases in magnitude and both corner (−6 dB) frequencies (F1 and F2) are shifted towards lower frequency range. Some examples of appropriate geometries of unfocused transducers are shown in FIG. 2B. Those are represented by a rectangular 205, cylindrical 206, and elliptical 207 shapes with aspect ratios $L_{min}:L_{max}$ of 5:6.

FIGS. 3A and 3B show two embodiments of the fluorescence imaging unit 106. The simpler, but less compact variant depicted in FIG. 3A has a wheel 301 with a set of fluorescence emission filters (not shown), which cover the emission spectra of studied fluorophores, while rejecting the spectrum of the optical excitation unit. The filter wheel could be rotated manually or using motorized remote control. Alternatively, it could be a single filter fixed in front or behind the image forming optics, which is installed inside the optical tube 302. The image forming optics is designed to produce planar projections of the interrogated object on the surface of an optical matrix sensor 303. Some appropriate alternatives of the sensor 303 include a charge-coupled device (CCD) and a complementary metal-oxide-semiconductor (CMOS) type camera sensors. Another variant of the fluorescence imaging unit is shown in FIG. 3B cut with a mid-vertical plane. It is the same type of detector as the one shown on the instrument assembly in FIG. 1C, allowing more compact implementation. In addition to the same components as those used in the embodiment shown in FIG. 3A including the filter wheel 301, the optical tube with imaging optics 302, and the camera sensor 303, there is an optical cube 304 with a 45° mirror 305 that bends the optical axis 306 of the fluorescence imaging unit by 90°, allowing its extended portion, incorporating the optical tube 302 and the camera sensor 303, to be oriented along the housing of the instrument (118 in FIG. 1C). An optical prism can be also used instead of the 45° mirror 305.

If the interrogated object is a small animal, it could be anesthetized and fixed in a restrainer 119, which is shown in FIG. 1C attached to a rotary mechanism 102 via a life support unit 120. The life support unit incorporates a breathing/gas anesthesia unit and, optionally, an intravenous injection unit and sensors for monitoring vital parameters of the interrogated animal.

Both the rotary mechanism 102 and the array of photoacoustic transducers are mounted on a top imaging plate 121. Such permanent arrangement of those two components minimizes chances of misalignment after multiple reloads of an interrogated object. The imaging tank 111 is permanently attached to the bottom imaging plate 122 forming a container capable of holding the coupling medium. The top imaging plate 121 is attached to the bottom imaging plate 122 via a lift mechanism 123, which is designed for moving the top imaging plate 121 in vertical direction. The lift mechanism may incorporate translation stages, poles and posts, bearings designed for smooth accurate linear movement, manual lift, and mechanical dampening elements. In its down-lock position (the lowest position, which is locked to prevent further accidental movement), the lift mechanism submerges the interrogated object and the array of photoacoustic transducers in the coupling medium inside the imaging tank. The down-lock position of the lift mechanism 123 is illustrated in FIG. 1C. In the down-lock position, the lift mechanism may also press the top imaging plate against the imaging tank, creating a gas-tight compartment above the level of the coupling medium. In that case, the gas-tight compartment will be further connected to the exhaust vent, which might be optionally enhanced with a vacuum line and appropriate gas filters. The gas-tight compartment with the exhaust vent is designed to prevent human exposure to the animal anesthesia gas, for example isoflurane, which is used in the instrument during imaging live small animal models. In its up-lock position (the highest position, which is locked to prevent further accidental movement), the lift mechanism pulls the interrogated object out of the coupling medium and fixes it in a position above the imaging tank such that it is convenient for an operator to quickly remove, set a new, or exchange the interrogated object. Due to prolonged exposures to warm moisture, it is preferable that the top and the bottom imaging plates are made of non-corrosive, rigid and durable materials, like hard plastics or fiberglass. Examples of such materials include Garolite or Micarta and polytetrafluoroethylene (Teflon). Generally, it is also preferable that the entire assembly of the instrument is done using parts and fixtures made of materials with reduced corrosive characteristics, for example, stainless steel, plastics, glass, and fiberglass. Also, during operation, the instrument must allow good ventilation of all components exposed to excessive moisture.

FIG. 4A shows a detailed 3D rendering of an embodiment for the object positioning mechanism that incorporates a motorized lift system 401 moving up and down the top imaging plate 121, a rotary stage 402 with embedded animal gas anesthesia line 403, and the animal restrainer 119. Accurate linear vertical motion of the top imaging plate is warranted by two guiding poles 404, connected to the top imaging plate over linear ball bearings 405. Each guiding pole is fixed to the bottom imaging plate 122 at one end, and to the top of the instrument's housing 406 at the other end, creating a rigid rail system.

FIG. 4B illustrates an exemplary design of the rotary mechanism assembly (mid-vertical section) showing a gas anesthesia line segment 407 that connects to a rotary stage adapter 408 over gas-tight rotary bearings 409. In such configuration, there is no torque transferred from the rotating stage 403 to the connecting anesthesia line segment 407, preventing entangling of the anesthesia line during imaging scans. The stage adapter 408 rotating together with the rotary stage 403, transfers torque to a hollow shaft 410, which is embedded into the stage adapter and is sealed with a gas-tight o-ring 411. During imaging scans, anesthesia gas is supplied to the gas anesthesia line, passes to the intermediate chamber 412, enters the hollow shaft 410, and, finally, moves inside the shaft towards the interrogated live small animal.

FIG. 4C shows an assembly scheme for a small animal (mouse) restrainer and a submersible breathing bell 413. The small animal restrainer consists of the top part 414 and the bottom part 415, which are assembled together along the guiding poles 416 and adjusted to accommodate the size of the interrogated animal. Two partial cylinders 417 and 418, which are the animal attachment sites, are designed such that the interrogated animal can easily grasp those with its front and hind legs, respectively. The appropriate diameters of those cylindrical parts should be between 10 and 20 mm for convenient position of a mouse. The animal attachment sites are fixed on the top and bottom crossbars 419 and 420, respectively. The main purpose of the crossbars is to increase rigidity of the restrainer and prevent its accidental deformations during imaging. A small animal (for example, a mouse) is fixed in the restrainer positioned on a lab bench or a table outside the imaging instrument by: (1) Assembling two parts of the restrainer to accommodate the length of the interrogated animal; (2) Placing the restrainer on a bench top or a custom pedestal (not shown) with cylindrical surfaces of the animal attachment sites 417 and 418 facing down and flat surfaces facing up; (3) Putting the anesthetized animal on top of the restrainer with front legs set around the proximal portion of the animal attachment site 417 (the one closer to the center of the restrainer with respect to the top crossbar 419) and hind legs set around the cylindrical portion of the part 418; at the same time, the head and the mouth of the animal must be rested on the distal flat portion of the animal attachment site 417 (the one father away from the center of the restrainer with respect to the top crossbar 419) and face forward towards the air-guiding groove 421; (4) Fixing the animal on the restrainer by wrapping an adhesive tape around the animal's body and the restrainer at the animal attachment sites 417 and 418. A vinyl electrical tape or an elastic band could be used to fix an animal in the restrainer. Black color of fixtures and elements of the restrainer is appropriate for fluorescence imaging, while white color is appropriate for photoacoustic imaging. When photoacoustic and fluorescence imaging are combined, it is best to use optically and acoustically transparent materials for animal fixing parts and accessories.

The submersible breathing bell 413 is designed for free breathing of an anesthetized interrogated animal, while it is fully submersed in the coupling medium. It operates similar to a diving bell by creating a slightly pressurized gas pocket inside its breathing chamber 422, when its top portion 423 with a gas-guiding channel (not shown) is connected to a gas line. The gas fills the breathing chamber 422 and is bubbling out from underneath the bell when the bell is submerged in the upward position (breathing chamber facing down and away from the free surface of the coupling medium). The animal restrainer is attached to the submersible breathing bell using a set of magnets or set screws and aligned, for example, over the notches 424. In such configuration the animal's mouth will be exposed to the anesthesia gas inside the breathing chamber 422 at all times during imaging with the instrument.

Two embodiments of the array of photoacoustic transducers are shown in FIG. 5. The benefits of an arc-shaped array 501, were discussed above and include: (1) the best detection characteristics as related to ability of each element of the array to see each voxel of an interrogated volume; (2) standard (spherical) tomographic reconstruction geometry. On the other hand, such array requires accurate alignment of its center and elevation tilt with respect to the axis of rotation. There are also constraints on a minimal radius and aperture of the sensitive arc 502 in such an array, which are dictated by requirements to accommodate an animal fixed in the restrainer. Larger radius of the array results in longer distances between some elements of the array (particularly those in the array's central part) and the voxels of interrogated volume emitting photoacoustic waves, which decreases sensitivity of those elements. An alternative embodiment 503 shows a linear arrangement of unfocused photoacoustic transducers along the sensitive surface of the array 504. Linear array can be moved much closer to the interrogated object extended along the axis or rotation (like a small animal in the restrainer) than the previously described arc array. Consequently, the linear configuration might champion better photoacoustic sensitivity, because a spherical photoacoustic wave is attenuated proportionally to the distance from its source. Simultaneously, the linear array configuration still produces a standard (cylindrical) tomographic reconstruction geometry, while tolerating misalignment of the distance to the axis of rotation better than the arc array tolerates misalignment of its center. When the distance from the linear array to the axis of rotation is compromised, the imaging scan will still produce a cylindrical set of positions for photoacoustic transducers where data was acquired. The image reconstruction algorithm will still be valid, just a new radius of cylindrical reconstruction geometry must be accurately evaluated. On the other hand, when the center of the arc array is misaligned with respect to the axis of rotation, it compromises the entire spherical reconstruction geometry. One significant disadvantage that linear array configuration might have as compared to the arc-shaped array configuration is in its inferior directionality (ability to sense photoacoustic waves approaching array elements from various locations inside the interrogated object). That becomes a particularly important aspect when the array is located close to the interrogated object, and elevation angles for incident photoacoustic waves (see FIG. 2A) become small.

Number of photoacoustic transducers in the array is constrained by the array's geometry and size, capabilities of the data acquisition unit, peripheral system, image reconstruction, and cost. Usually, the more transducers are implemented in the photoacoustic array, the finer image quality could be obtained. Often, it is necessary to further process the parallel photoacoustic data acquired from all transducers of the array. Many signal processing algorithms utilize Fast Fourier Transform (FFT), which is the most efficient, when the amount of data to be processed is a power of two. Therefore, in some embodiments, it may be important to keep number of photoacoustic transducers in the array equal to a power of two.

Three embodiments 601-603 of a multi-bandwidth photoacoustic transducer array are shown in FIG. 6A. A linear arrangement of the array's elements is provided for illustrative purposes. Other configurations, such as arc-shaped which were discussed above, can be similarly constructed. The lighter rectangles 604 represent transducers, which are the most responsive to low- and medium-frequency (LF) photoacoustic signals (normally, below 2 MHz). The darker rectangles 605 represent transducers, which are the most responsive to medium- and high-frequency (HF) photoacoustic signals (normally, above 0.5 MHz). For illustration, typical spectral sensitivities of LF and HF photoacoustic transducers are diagrammed on the inlet 606. The shown LF transducer is the most sensitive for photoacoustic waves with major frequency content in the range [F1L F2L]. The shown HF transducer is the most sensitive for photoacoustic waves with major frequency content in the range [F1H F2H]. The elements should produce essentially similar spatial acousto-electric responses for the medium-frequency range of photoacoustic signals. The array 601 is composed of two LF and HF sub-arrays stacked sequentially, such that the last element of one sub-array is followed by the first element of the other sub-array. The array 602 is composed of two sub-arrays with alternating LF and HF elements. The array 603 is composed of two parallel sub-arrays with LF and HF elements. The arrays are designed and arranged such that every element of each sub-array can sense photoacoustic waves generated at any location inside the interrogated object. Such multi-frequency implementation of a photoacoustic array with separate DAQ channels optimized for individual sub-arrays provides the following significant benefits. (1) It enables extension of the spectral sensitivity bandwidth of photoacoustic detection to the limits of combined sensitivity bandwidth of sub-arrays. Since all photoacoustic waves are detected as broad-band signals, it is extremely important to have photoacoustic detection bandwidth as wide as possible. Therefore, combining photoacoustic transducers with high sensitivities in different regions of the spectrum (like LF and HF) would be equivalent to extending photoacoustic detection bandwidth for the entire array. (2) Separating detected photoacoustic data into individual LF and HF channels allows very efficient utilization of the entire dynamic range of the DAQ unit. Most of photoacoustic waves are detected as bipolar signals, which have a sin c(w)=sin(w)/w type distribution of frequency components w. Therefore, significant amount of energy and information carried by photoacoustic signals is contained in the LF domain. Larger photoacoustic sources, like internal organs and the entire animal's body, generate high-energy LF components, which may easily mask low-energy HF components representing fine features of photoacoustic sources, like blood vessels and photoacoustic boundaries. If a single DAQ unit is used to detect both types of photoacoustic signals with a fixed amplification, the smaller photoacoustic signatures could get lost in noise. FIG. 6B illustrates an embodiment that separates detection and processing of LF and HF photoacoustic signal components to provide optimal utilization of dynamic range of a single analog-to-digital converter (ADC). The original photoacoustic waveform 607 contains a large low frequency signal (LF PA signal) and much smaller high frequency signal (HF PA signal), riding on top of the LF PA signal. The original photoacoustic waveform is detected by LF and HF transducers connected to the corresponding LF and HF amplification circuitries and forming separate LF and HF channels 608 and 609. The channels are tuned so that on the output, both LF PA signal 610 and HF PA signal 611 will have approximately the same magnitudes, high signal-to-noise ratios, and could be digitized by a single ADC with equal accuracies.

FIG. 7A provides an electric schematics with the thermal noise level equivalent to that generated in a single photoacoustic detection channel when represented by the intrinsic capacitance (C1) of the sensitive photoacoustic element 701 and the input impedance (R1) of the photoacoustic amplifier 702. In that schematics, the photoacoustic amplifier is connected to the sensitive photoacoustic element over a short electric transmission line 703. In practice, a short electric transmission line can be implemented by, for example, integrating a photoacoustic amplifier inside the photoacoustic transducer array next to the corresponding sensitive photoacoustic element. The short electric transmission line 703 has the resonant frequency, which is well above frequency bandwidths of both the photoacoustic amplifier and the ADC. The mean square voltage noise at the input of photoacoustic amplifier integrated over the frequency bandwidth can be calculated as $V^2=k_B \cdot T/C1$, where $k_B$ is the Boltzmann's constant, T is the absolute temperature of the photoacoustic detection channel. Therefore, the voltage noise level does not depend on the value of the input impedance R1. The top corner frequency for the noise spectrum generated by the circuit shown in FIG. 7A is $1/(4 \cdot R1 \cdot C1)$. High values of the input impedance R1 shift the noise spectrum to the low frequency range; the increased level of the low frequency noise can be filtered out using high pass filters inside the photoacoustic amplifier or the ADC. Typical values of the capacitance C1 are in the range of 10-200 pF. Typical values of the input impedance R1 are in the range of 1-1000 kΩ. In practice, the value of input impedance R1 is restricted by transmission line effects, discussed in the next paragraph, and input impedance of the first amplification stage, represented, for example, by a FET transistor, an operational amplifier, or a custom integrated circuit.

FIG. 7B illustrates an embodiment of a single photoacoustic detection channel with the photoacoustic sensitive element 701 spatially separated from the photoacoustic amplifier 702 by a long transmission line 704 with complex impedance Z1. In practice, a long electric transmission line can be implemented by, for example, connecting a sensitive photoacoustic element with a photoacoustic amplifier using a coaxial cable. The resonant frequency of such long transmission line is $f_{LONG}=0.7 \cdot c/4L$, where L is the wiring length; 0.7 is the typical velocity factor for a coaxial cable; and c is the speed of light in vacuum. For example, a two-meter long coaxial cable has the quarter-wavelength resonant frequency of 26 MHz, which is within working bandwidth of some high-frequency photoacoustic transducers. Therefore, electrical characteristics (Z1) of such transmission line have to be incorporated into the overall electrical model of the photoacoustic detection channel. Voltage standing wave ratio (VSWR) for such transmission line is significantly different from 1 at both ends: The termination at the sensitive photoacoustic element 701 has low impedance with negative reflection coefficient F close to −1, while the termination at the input of photoacoustic amplifier has high impedance with positive reflection coefficient Γ close to +1. Impedance mismatch at both ends transforms the transmission line into a resonator, which is immune to the electromagnetic interference (EMI). EMI effects can be further suppressed by electromagnetic shielding, decreasing the input impedance of photoacoustic amplifier, and reducing the length of the transmission line.

FIG. 8 provides a diagram that explains design and operation of the DAQ unit. Boxes represent DAQ components, as well as other units and sensors. Double arrows indicate data flow, while single arrows indicate parameter setting/reading. Solid boundaries and arrows mark mandatory components and processes, while dashed boundaries and arrows mark optional components and processes. A standard configuration of DAQ allows synchronized optical excitation 801 (in this case by a laser), collection of photoacoustic data 802 and 803, and collection of fluorescence images 804. A small portion of optical excitation is used to measure characteristics of optical pulses—the pulse onset and the pulse energy. That data is collected by a Laser Pulse Meter and is transferred 805 to the DAQ's portion responsible for Laser Pulse Measurements (LPM). Specifically, the pulse onset is used to trigger acquisition of photoacoustic data, which sometimes needs to be delayed in order to start data collection when first photoacoustic waves generated inside the interrogated object arrive to the PA array, and avoid photoacoustic artifacts, which are often present at the time of the optical irradiation and could last for a few microseconds. The trigger initiating acquisition of a fluorescence image 804 may precede laser pulses to allow for complete opening of the camera shutter. DAQ is used to control the exposure of fluorescence detector (FEC). The information on pulse energy is later used in quantitative PAT and FMT. Another mandatory feature of the DAQ is the angular position control (APC). It sends commands to the rotary stage allowing it to start a scan, move with preset angular steps or constant velocity, pause for data acquisition at a defined position, and finalize the scan.

DAQ may be optionally configured to perform the following. (1) Control the output energy (LEC) and wavelength (LWC) of optical excitation pulses. LEC serves primarily to optimize dynamic range of acquired photoacoustic signals. DAQ or a peripheral computational system will continuously analyze acquired photoacoustic data, and the DAQ will actively modify the energy of optical excitation pulses to match the scale of received photoacoustic signals to the scale of the ADC. LEC channel may be also used to boost energy of fluorescence excitation, when there is not enough sensitivity for the studied fluorophore. DAQ may also employ another optional channel with variable gain control (VGC) of the photoacoustic amplifier (PA amplifier) for additional manipulation of the magnitude of acquired photoacoustic signals and accommodation of the ADC's full dynamic range. LWC channel may be utilized between individual imaging scans or within each scan to manipulate those excitation sources which allow external control of their optical wavelengths. Performing imaging scans at both excitation and emission wavelengths of a studied fluorophore is necessary for some FMT reconstruction algorithms, which use more accurate experimentally-built photon propagation model. Also, multiwavelength imaging scans are always necessary when more than one fluorophore is studied in the same set of imaging scans or when multi-wavelength photoacoustic spectral unmixing algorithms are implemented for imaging. (2) If more accurate knowledge of angular position of the interrogated object is required, a dedicated encoder can be used along with the rotary stage 806. The angular position measured by the encoder is transferred to the DAQ's channel dedicated to the angular position measurement (APM), and can be further used in a feedback control (APC) of the rotary stage. (3) The imaging instrument may be optionally equipped with additional sensors. Examples of important external sensors include sensors of vital parameters and environmental temperature sensors. A sensor of vital parameters is used for evaluation of vital signs and physiological conditions of the interrogated small animal. Some examples include: (a) camera, which allows visual observation of the animal, its motion, and breathing during an imaging scan; (b) breathing monitor, which may be a pressure or flow sensor incorporated into an anesthesia/breathing line and measuring variations associated with breathing of the interrogated animal; (c) electrocardiography unit, allowing to monitor heart activity; (d) body temperature monitor; (e) pulse oximeter, measuring oxygenation levels of arterial blood. Environmental temperature sensors, like thermocouples, are installed inside the imaging tank and provide continuous temperature readings from various points inside the coupling medium. Accurate knowledge of temperature inside the coupling medium allows to appropriately adjust speed of sound of the coupling medium during photoacoustic image reconstruction and to maintain high fidelity of the resultant images. Measurement and control of temperature inside the coupling medium is also crucial in imaging live anesthetized animals, which requires a fairly narrow range 30-38° C. to be maintained at all times when animal is submerged inside the coupling medium. Sensors of vital parameters and temperature sensors communicate with ADC via corresponding channels (VPM) and (TMP), respectively. (4) There are few optional upgrades allowing DAQ to control fluorescence imaging unit. Emission wavelength control (EWC) is designed to enable automatic adjustment of the spectral sensitivity to match the emission spectrum of a studied fluorophore. One of the ways to achieve that is to implement a motorized optical filter wheel 301 (FIGS. 3A and 3B). Autofocusing of the imaging optics (AFC) is implemented to guarantee sharp fluorescence images of the interrogated object at any position of the interrogated object. Control of the dynamic range of fluorescence detector (FDC) is necessary for enabling registration of fluorescence sources with dramatically different intensities. It can be achieved by upgrading fluorescence imaging unit with another motorized optical filter wheel populated with neutral density filters or by direct adjustment of the sensitivity of fluorescence detectors.

The DAQ can be further configured for communication with a processing unit (Processor), which processes acquired fluorescence and photoacoustic data and uses the processed data to reconstruct images of the interrogated object. In such configuration the Processor can be physically integrated with the entire instrument and communicate using a local protocol (e.g. USB 2.0, USB 3.0, USB Type-C, PCI Express, FireWire or Ethernet). Alternatively, the instrument can communicate with a Processor remotely using, for example, TCP/IP or other remote communication protocol. The Processor can be further configured to communicate with a display unit (Display) providing visualization of the reconstructed photoacoustic and fluorescence images. Examples of the Display include a 2D or a 3D monitor, a mobile device or a virtual reality system. The Display may be also a remote terminal communicating with the Processor over a TCP/IP or other remote communication protocol.

FIG. 9 provides a set of diagrams describing various methods for acquiring co-registered fluorescence and photoacoustic orthogonal projections of the interrogated object using embodiments of the imaging instrument, which were described above.

FIG. 9A provides an algorithm for acquiring co-registered fluorescence and photoacoustic orthogonal projections of the interrogated object, which is rotated by a rotary mechanism in discrete angular steps. The algorithm comprises the following steps to be performed either by a user of the imaging instrument or automatically by the DAQ or the Processor. First step: Establish a set of imaging parameters with the DAQ unit 901. The required parameters include: optical excitation spectrum (wavelength) $\lambda$ex adequate for excitation of the studied fluorophore(s); detection parameters of the fluorescence imaging unit $S_{FL}$, including spectral sensitivity, covering the emission spectrum of the studied fluorophore(s), and the detector's exposure; number of photoacoustic $N_{aq}$(PA) and fluorescence $N_{aq}$(FL) frames to be acquired at each discrete angular position of the rotary mechanism; an angular step $ROT_{stop}$ used by the rotary mechanism during imaging scan; criterion for the scan stop $ROT_{stop}$ (usually it is completion of a full 360° rotation circle, but could be less or more than 360°). Second step: Turn on the primary (pulsed) and any secondary (pulsed or CW) optical excitation units 902. Third step: Start the imaging scan and acquire required number of photoacoustic $N_{aq}$(PA) and fluorescence $N_{aq}$(FL) frames 903. Optionally, the optical excitation spectrum and/or the detection parameters of fluorescence imaging unit $S_{FL}$ could be changed and data acquisition repeated 904. Sweeping optical excitation and/or fluorescence detection for each angular position of the interrogated object allows to acquire co-registered multispectral photoacoustic and fluorescence orthogonal projections, which can be later used for building advanced FMT photon propagation model of the interrogated object or for performing photoacoustic spectral unmixing. The acquired data may be further processed by or internally saved in the DAQ or transferred to a peripheral system. Fourth step: Rotate the interrogated object using rotary mechanism by the angular step $ROT_{stop}$ 905 and repeat the steps 3 and 4 until scan stop condition $ROT_{stop}$ is encountered 906.

FIG. 9B provides an algorithm for acquiring co-registered fluorescence and photoacoustic orthogonal projections of the interrogated object, which is rotated by a rotary mechanism in continuous motion. The algorithm comprises the following steps to be performed either by a user of the imaging instrument or automatically by the DAQ or the Processor. First step: Establish a set of imaging parameters with the DAQ unit 907. The required parameters include: optical excitation spectrum (wavelength) $\lambda_{ex}$ adequate for excitation of the studied fluorophore(s); detection parameters of the fluorescence imaging unit $S_{FL}$, including spectral sensitivity, covering the emission spectrum of the studied fluorophore(s), and the detector's exposure; angular velocity $ROT_{speed}$ used by the rotary mechanism during imaging scan; criterion for the scan stop $ROT_{stop}$ (usually it is completion of a full 360° rotation circle, but could be less or more than 360°; it could also be limited by time duration of the imaging scan). Second step: Turn on the primary (pulsed) and any secondary (pulsed or CW) optical excitation units 902. Third step: Start the imaging scan by initiating continuous rotation of the interrogated object with angular velocity $ROT_{speed}$ 908. Fourth step: Continue acquiring photoacoustic and fluorescence frames, each labeled with the current angular position of the interrogated object, until the scan stop condition $ROT_{stop}$ is encountered 909. The acquired data may be further processed by or internally saved in the DAQ or transferred to a peripheral system. Optionally, a sweep of excitation or fluorescence detection parameters may be implemented similar to that described above for the step-wise rotational scans, while continuously rotating the interrogated object and acquiring photoacoustic and fluorescence data. If the angular velocity $ROT_{speed}$ is selected to be small enough, a single 360° rotational scan may be sufficient to collect data at required number of angular positions of the interrogated object for every set of excitation/emission detection parameters. Alternatively, scans covering more than 360° can be also performed.

FIG. 9C provides an algorithm for acquiring photoacoustic surface (skin) projections of the interrogated object, which is rotated by a rotary mechanism in discrete angular steps. Acquisition of photoacoustic skin data may accompany acquisition of orthogonal photoacoustic and fluorescence projections of an interrogated object in order to provide anatomical reference and further inform an FMT photon propagation model. The algorithm comprises the following steps to be performed either by a user of the imaging instrument or automatically by the DAQ or the Processor. First step: Establish a set of imaging parameters with the DAQ unit 910. The required parameters include: optical excitation spectrum (wavelength) $\lambda_{skin}$ adequate for initiation of photoacoustic effect in a superficial layer (skin) of the interrogated object; number of photoacoustic skin frames $N_{aq}(PA_{skin})$ to be acquired at each discrete angular position of the rotary mechanism; an angular step $ROT_{stop}$ used by the rotary mechanism during photoacoustic skin scan; criterion for the skin scan stop $ROT_{stop}$ (usually it is completion of a full 360° rotation circle, but could be less or more than 360°). Second step: Turn on the pulsed photoacoustic skin excitation unit 911. Third step: Start the photoacoustic skin scan and acquire required number of photoacoustic skin frames $N_{aq}(PA_{skin})$ 912. The acquired photoacoustic skin data may be further processed by or internally saved in the DAQ or transferred to a peripheral system. Fourth step: Rotate the interrogated object using rotary mechanism by the angular skin step $ROT_{stop}$ 913 and repeat the steps 3 and 4 until skin scan stop condition $ROT_{stop}$ is encountered 914.

FIG. 9D provides an algorithm for acquiring photoacoustic skin projections of the interrogated object, which is rotated by a rotary mechanism in continuous motion. The algorithm comprises the following steps to be performed either by a user of the imaging instrument or automatically by the DAQ or the Processor. First step: Establish a set of imaging parameters with the DAQ unit 915. The required parameters include: optical excitation spectrum (wavelength) $\lambda_{skin}$ adequate for initiation of photoacoustic effect in a superficial layer (skin) of the interrogated object; angular velocity $ROT_{speed}$ used by the rotary mechanism during the skin scan; criterion for the skin scan stop $ROT_{stop}$ (usually it is completion of a full 360° rotation circle, but could be less or more than 360°; it could also be limited by time duration of the skin scan). Second step: Turn on the pulsed photoacoustic skin excitation unit 911. Third step: Start the photoacoustic skin scan by initiating continuous rotation of the interrogated object with angular velocity $ROT_{speed}$ 916. Fourth step: Continue acquiring photoacoustic skin frames, each labeled with the current angular position of the interrogated object, until the skin scan stop condition $ROT_{stop}$ is encountered 917. The acquired skin data may be further processed by or internally saved in the DAQ or transferred to a peripheral system.

FIG. 10 provides a set of diagrams describing methods, which can be used for reconstruction of images of an interrogated object from acquired orthogonal photoacoustic and fluorescence projections.

FIG. 10A illustrates a method for reconstructing images of spatial distribution of a fluorophore inside an interrogated object using acquired co-registered orthogonal fluorescence and photoacoustic projections. A set of orthogonal fluorescence projections is acquired while the fluorescence imaging unit is configured for exclusive sensitivity of the emission spectrum of the studied fluorophore 1001. Another set of orthogonal fluorescence projections may be optionally acquired while the fluorescence imaging unit is configured for exclusive sensitivity of the excitation spectrum of the studied fluorophore. A set of orthogonal photoacoustic projections is acquired while the optical excitation unit is configured to emit the spectrum, which is essentially similar to the excitation spectrum of the studied fluorophore 1002. The photoacoustic projections are used in a PAT algorithm 1003, which is modified to recover volumetric distribution of fluence 1004 inside the interrogated object irradiated by the optical excitation unit. In a particular embodiment of the imaging instrument employing a multi-bandwidth composite photoacoustic array, the data collected with low frequency sub-array may be used to reconstruct volumetric distribution of optical fluence inside the interrogated object. Finally, the volumetric distribution of the studied fluorophore 1007 inside the interrogated object is recovered from the acquired orthogonal fluorescence projections 1001 by using an FMT reconstruction algorithm 1006 with emission-only photon propagation model PPM($\lambda$em) constructed for the interrogated object 1005 using, for example, representative values of the optical parameters for various tissues and organs. The excitation portion of the photon propagation model directly employs the obtained distribution of optical fluence at the excitation spectrum of the studied fluorophore 1004.

The algorithm, outlined in FIG. 10A may optionally employ an additional set of orthogonal photoacoustic projections acquired while the optical excitation unit is configured to emit the spectrum, which is essentially similar to the emission spectrum of the studied fluorophore 1008. In that case, the photoacoustic projections acquired for the emission spectrum of the studied fluorophore are used in a PAT algorithm 1009, which is now modified to evaluate volumetric distribution of optical absorption coefficient $MIU_a$ ($\lambda_{em}$) at the emission spectrum of the studied fluorophore 1010. The found map of $MIU_a(\lambda_{em})$ is further used to inform the PPM($\lambda_{em}$) constructed for the interrogated object 1005.

FIG. 10B illustrates another method for reconstructing images of spatial distribution of a fluorophore inside an interrogated object using acquired co-registered fluorescence and photoacoustic orthogonal projections, as well as photoacoustic skin projections. Acquisition of orthogonal fluorescence and photoacoustic projections and their implementation in the image reconstruction algorithm is similar to that described above and illustrated in FIG. 10A. Briefly, a set of orthogonal fluorescence projections is acquired while the fluorescence imaging unit is configured to cover exclusively the emission and/or the excitation spectra of the studied fluorophore 1001. A set of orthogonal photoacoustic projections is acquired while the optical excitation unit is configured to emit the spectrum, which is essentially similar to the excitation spectrum of the studied fluorophore 1002, and then the PAT algorithm 1003 is used to recover volumetric distribution of fluence 1004 inside the interrogated object irradiated by the optical excitation unit. Additionally, the PAT algorithm 1009 is used to evaluate volumetric distribution of optical absorption coefficient $MIU_a$ and construct an optical segmentation model SEGM 1013, which consists of connected volumetric segments having essentially different optical absorption coefficients. The optical segmentation model 1013 is further informed by a two-domain geometric segmentation (inside/outside the interrogated object) extracted using photoacoustic tomography 1012 of the acquired photoacoustic skin projections 1011. The orthogonal fluorescence projections 1001 and volumetric distribution of fluence 1004 are further used in an emission-only FMT reconstruction algorithm 1014 built on the complete optical segmentation model 1013, recovering the volumetric distribution of the studied fluorophore 1007 inside the interrogated object.

FIG. 10C illustrates yet another method for reconstructing images of spatial distribution of a fluorophore inside an interrogated object using acquired co-registered fluorescence and multi-spectral photoacoustic orthogonal projections. This method relies on high SNR of photoacoustic signals generated by the studied fluorophore, and is generally to be applied when local concentrations of the studied fluorophore inside the interrogated object are expected to be relatively large. The method employs orthogonal fluorescence projections 1001 and uses them as inputs with any reconstruction algorithm 1015 (including an FMT-based algorithm) enabling approximate volumetric imaging of the studied fluorophore. The photoacoustic orthogonal projections 1016 are acquired with the optical excitation unit configured to emit various spectra $\lambda_i$, including at least one spectrum, which is essentially similar to the excitation spectrum of the studied fluorophore $\lambda$ex. A PAT algorithm 1017 is used with each orthogonal photoacoustic projection $PAT(\lambda_i)$ to recover volumetric data characterizing optical energy absorbed inside the interrogated object, which was illuminated by the optical excitation unit configured to emit the corresponding spectra $\lambda_i$. Finally, the accurate high-resolution volumetric image 1007 of the fluorophore is reconstructed with a photoacoustic spectral unmixing algorithm 1018, which is modified to accommodate spatial constraints imposed by the approximate volumetric image(s) of the fluorophore reconstructed from the acquired orthogonal fluorescence projections 1001.

At least some aspects disclosed can be embodied, at least in part, in software. That is, the techniques may be carried out in a special purpose or general purpose computer system or other data processing system in response to its processor, such as a microprocessor, executing sequences of instructions contained in a memory, such as ROM, volatile RAM, non-volatile memory, cache or a remote storage device. Functions expressed in the claims may be performed by a processor in combination with memory storing code and should not be interpreted as means-plus-function limitations.

Routines executed to implement the embodiments may be implemented as part of an application, operating system, firmware, ROM, middleware, service delivery platform, SDK (Software Development Kit) component, web services, or other specific application, component, program, object, module or sequence of instructions referred to as "computer programs." Invocation interfaces to these routines can be exposed to a software development community as an API (Application Programming Interface). The computer programs typically comprise one or more instructions set at various times in various memory and storage devices in a computer, and that, when read and executed by one or more processors in a computer, cause the computer to perform operations necessary to execute elements involving the various aspects.

A machine-readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer-to-peer networks. Different portions of the data and instructions can be obtained from different centralized servers and/or peer-to-peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine-readable medium in entirety at a particular instance of time.

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROMS), Digital Versatile Disks (DVDs), etc.), among others.

In general, a machine readable medium includes any mechanism that provides (e.g., stores) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

As used herein, and especially within the claims, ordinal terms such as first and second are not intended, in and of themselves, to imply sequence, time or uniqueness, but rather are used to distinguish one claimed construct from another. In some uses where the context dictates, these terms may imply that the first and second are unique. For example, where an event occurs at a first time, and another event occurs at a second time, there is no intended implication that the first time occurs before the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristic.

What is claimed is:

1. An instrument for acquiring co-registered orthogonal fluorescence and photoacoustic volumetric projections, comprising:
   an imaging tank filled with liquid, the liquid comprising
      a coupling medium selected from the group consisting of: a single chemical, mixture, solution, suspension, emulsion or gel;

an object positioning mechanism configured to position an interrogated object, or part thereof, inside the coupling medium in the tank and to rotate the interrogated object about a rotation axis relative to the tank;

an optical excitation unit fixed with respect to the tank and configured to induce both fluorescence and photoacoustic responses inside the interrogated object using the same optical excitation spectrum and the same irradiation pattern at the surface of the interrogated object, with light-emitting outputs arranged so as to illuminate two opposite sides of the interrogated object at each of a plurality of rotational positions of the interrogated object;

an array of unfocused photoacoustic transducers fixed with respect to the tank, each element of the array configured to detect photoacoustic signals generated inside the interrogated object, the array being arranged such that a plane connecting the rotation axis and a central portion of the array cuts through the interrogated object separating the two sides irradiated by the optical excitation unit;

at least one optical detector fixed with respect to the tank, configured to register planar projections of sources of fluorescence generated inside the object, and arranged opposite to the array of photoacoustic transducers with respect to the interrogated object; and, a data acquisition unit configured to synchronize acquisition of photoacoustic data, acquisition of fluorescence data, optical excitation, and rotational position of the interrogated object;

the instrument being further configured to amplify, filter, digitize, and transfer acquired data to a peripheral system for subsequent storage, processing, or visualization.

2. The instrument of claim 1 wherein the coupling medium has (a) specific acoustic impedance of $1.1 \times 10^6$ to $1.8 \times 10^6$ kg/(m$^2$*s), and (b) optical absorption coefficient and effective optical attenuation coefficient of 0 to 0.2 cm$^{-1}$ each for wavelengths employed by the optical excitation unit.

3. The instrument of claim 1 wherein the object positioning mechanism comprises a rotary stage that rotates the interrogated object, the rotary stage being operated in a continuous mode or a stepper mode with an encoder measuring angular position of the interrogated object at each of a plurality of photoacoustic and fluorescence data acquisition events.

4. The instrument of claim 1 wherein the object positioning mechanism incorporates an animal restrainer and a life support unit with a breathing unit, a gas anesthesia unit, or an intravenous delivery unit.

5. The instrument of claim 4 wherein the breathing or gas anesthesia is delivered to the interrogated object inside the coupling medium via a submersible positive pressure breathing bell mechanism.

6. The instrument according to claim 3 or 5, further comprising a pipe configured to deliver a breathing and anesthesia gas mixture, the pipe remaining static while an animal is rotated.

7. The instrument of claim 1 wherein the light-emitting outputs comprise fiberoptic termini either submerged into the coupling medium or externally attached to the optically transparent portion of the imaging tank via optically transparent index-matching fluid, gel, or adhesive.

8. The instrument of claim 1 wherein the optical excitation unit is configured to operate at one or more wavelengths in the range of 532 nm to 1400 nm, to produce pulses with an arbitrary temporal pulse profile and pulse duration of less than 100 ns as estimated at full-width-half-max, and to produce the pulses at a pulse repetition rate exceeding 0.5 Hz.

9. The instrument of claim 8 wherein the optical excitation unit comprises one or more of the following sources of radiation synchronized to emit simultaneous pulses: Q-switched Nd:YAG lasers, Ti:Saph lasers, Alexandrite lasers, optical parametric oscillators or pulsed diode lasers.

10. The instrument of claim 8 additionally configured to have the second optical excitation unit employing continuous wave illumination with the same spectral content and irradiation pattern at the surface of the interrogated object as the pulsed optical excitation unit.

11. The instrument of claim 1 additionally configured to have a continuous wave optical illumination unit that operates in a visible spectral range of 400-700 nm and together with the optical detector provides for visual observation of the interrogated object.

12. The instrument of claim 1 additionally configured to have a pulsed optical excitation unit fixed with respect to the tank that operates in a visible spectral range of 400-700 nm and is further configured to induce photoacoustic response inside a superficial layer of the interrogated object that is facing the array of photoacoustic transducers.

13. The instrument of claim 1 wherein the array of photoacoustic transducers comprises first and second sub-arrays having identical elements except that the elements of the first array are the most sensitive to ultrasound frequencies below 2 MHz and the elements of the second array are the most sensitive to ultrasound frequencies above 0.5 MHz, each of the first and second sub-arrays having its own data acquisition unit designed to match spectral bandwidth of the transducer elements of the sub-array and provide appropriate gain for a complete utilization of dynamic range of a digitizer.

14. The instrument of claim 13 wherein the first and second sub-arrays are arranged in parallel to each other, are sequentially stacked, or comprise a single array with alternating elements of each particular sub-array.

15. The instrument of claim 1 wherein the optical detector comprises an optical filter that rejects one or more wavelengths employed by the optical excitation unit while passing one or more wavelengths emitted by a fluorophore of interest.

16. The instrument of claim 1 wherein the interrogated object is live and the data acquisition unit is further configured to perform monitoring of vital parameters of the interrogated object.

17. The instrument of claim 1 wherein the data acquisition unit is further configured to perform monitoring of the output optical energy of the optical excitation unit.

18. The instrument of claim 17 wherein the data acquisition unit is further configured to perform automatic adjustment of dynamic range of measured photoacoustic data to match that of a digitizer, the adjustment being performed by regulation of output optical energy and/or amplification of detected photoacoustic signals.

19. The instrument of claim 1 wherein the data acquisition unit is further configured to control an emitted spectrum of the optical excitation unit.

20. The instrument of claim 1 wherein the data acquisition unit is further configured to control exposure, spectral sensitivity, focusing, and dynamic range of the optical detector.

21. The instrument of claim 1 wherein all the components of the instrument outside the imaging tank which are exposed to the radiation from the optical excitation unit are transparent or pitch-black to minimize background fluorescence and stray light.

22. The instrument of claim 1 wherein the object positioning mechanism is equipped with a lift system which in an up-lock position fixes the interrogated object outside the coupling medium so as to allow for rapid reload.

23. The instrument of claim 1 further configured such that the data acquisition unit communicates with a processing unit that processes fluorescence data and photoacoustic data and uses the fluorescence data and photoacoustic data to reconstruct images of the interrogated object.

24. The instrument of claim 23 wherein the processing unit is a remote computer server communicating with the data acquisition unit over a TCP/IP or other remote communication protocol.

25. The instrument of claim 23 further configured such that the processing unit communicates with a display unit to provide visualization of the interrogated object using reconstructed images, the display unit comprising a 2D or 3D monitor, mobile device or a virtual reality system.

26. The instrument of claim 25 wherein the processing unit is a remote computer server and the display unit is a remote terminal communicating with the processing unit over a TCP/IP or other remote communication protocol.

27. The instrument of claim 1 wherein input impedance of each photoacoustic amplifier channel is matched to an impedance of a corresponding sensing element of the array of photoacoustic transducers according to a frequency bandwidth of a particular photoacoustic detection channel.

28. A method for using the instrument recited in claim 1 to collect co-registered photoacoustic and fluorescence orthogonal projections of an interrogated object comprising:
   configuring an optical excitation unit to emit a radiation spectrum that can excite at least one of a plurality of fluorophores inside an interrogated object;
   configuring an optical detector to be sensitive only to an emission spectrum of the at least one fluorophore;
   using the optical excitation unit to irradiate the interrogated object while collecting a plurality of fluorescence and photoacoustic frames;
   rotating the interrogated object by a preset angular step and repeating the step of using the optical excitation unit to irradiate the interrogated object while collecting a second plurality of fluorescence and photoacoustic frames;
   repeating the above step until the interrogated object has been rotated by a predetermined angle; and,
   repeating the above steps with the optical excitation and detection units configured for each of the plurality of fluorophores.

29. The method of claim 28 wherein the interrogated object is rotated and the data is acquired continuously, and wherein each acquired packet of data further includes a current angular position of the interrogated object.

30. The method of claim 28 or claim 29 wherein the instrument is used to collect co-registered orthogonal photoacoustic and fluorescence projections as well as photoacoustic skin data from the interrogated object by performing two sequential scans in any order:
   with the optical excitation unit on and a photoacoustic skin excitation unit off, acquiring both fluorescence and photoacoustic data;
   with the optical excitation unit off and the photoacoustic skin excitation unit on, acquiring only photoacoustic data.

31. The method of claim 30, wherein the instrument is configured to reconstruct images using fluorescence molecular tomography built on an emission-only photon propagation model and using as input volumetric distribution of optical fluence at the excitation spectrum of the fluorophore, the fluence obtained by photoacoustic tomography from acquired photoacoustic orthogonal projections, and wherein multi-domain optical segmentation is further utilized in the photon propagation model, the multi-domain optical segmentation being provided by the photoacoustic tomography of the acquired photoacoustic orthogonal and skin projections.

32. The method of claim 28 or claim 29 wherein the instrument is used to collect co-registered fluorescence and multi-wavelength photoacoustic orthogonal projections of the interrogated object by performing multiple sequential scans while at each scan operating the optical excitation unit at different optical spectrum, at least one of the spectra overlapping by 50% or more with an excitation spectrum of the investigated fluorophore.

33. The method of claim 32 wherein at least one spectrum emitted by the optical excitation unit overlaps by at least 50% with the emission spectrum of the investigated fluorophore.

34. The method of claim 28 wherein the instrument is used to collect co-registered multi-wavelength fluorescence and photoacoustic orthogonal projections of the interrogated object by performing a single scan while sweeping an optical spectrum of the optical excitation unit at each angular position of the interrogated object, with a sweep range including a portion of the excitation spectrum of the studied fluorophore.

35. The method of claim 32 or claim 34, wherein image reconstruction utilizes a photoacoustic spectral unmixing algorithm spatially constrained to the fluorescent volumes reconstructed using the fluorescence data.

36. The method of claim 34 wherein the sweep range includes a portion of the excitation spectrum and a portion of emission spectrum of the studied fluorophore.

37. The method of claim 28 or claim 29, wherein image reconstruction is performed by fluorescence molecular tomography built on an emission-only photon propagation model and using as input volumetric distribution of optical fluence at the excitation spectrum of the fluorophore, the fluence obtained by photoacoustic tomography from the acquired photoacoustic orthogonal projections.

38. The method of claim 37, wherein the emission-only photon propagation model is further informed by volumetric distribution of an optical absorption coefficient inside the interrogated object, the volumetric distribution being estimated from photoacoustic orthogonal projections acquired while the optical excitation unit is configured for an emission spectrum of the studied fluorophore.

39. The method of claim 37, wherein the instrument is configured to collect the photoacoustic orthogonal projections with the low-frequency sub-array and use the projections to reconstruct volumetric distribution of optical fluence inside the interrogated object.

* * * * *